(12) United States Patent
Moriyama

(10) Patent No.: US 6,842,705 B2
(45) Date of Patent: Jan. 11, 2005

(54) GAS FLOW RATE MEASURING DEVICE AND GAS FLOW RATE MEASURING METHOD

(75) Inventor: Akinobu Moriyama, Yokohama (JP)

(73) Assignee: Nissan Motor Co., Ltd., Yokohama (JP)

( * ) Notice: Subject to any disclaimer, the term of this patent is extended or adjusted under 35 U.S.C. 154(b) by 0 days.

(21) Appl. No.: 10/636,710

(22) Filed: Aug. 8, 2003

(65) Prior Publication Data

US 2004/0035219 A1 Feb. 26, 2004

(30) Foreign Application Priority Data

Aug. 22, 2002 (JP) ........................................ 2002-242316
Feb. 14, 2003 (JP) ........................................ 2003-037014

(51) Int. Cl.$^7$ ................................................ G01F 1/00
(52) U.S. Cl. .................. 702/45; 73/861.04; 73/861.42; 204/424; 204/425
(58) Field of Search ............................. 702/45, 49, 50, 702/100; 73/23.32, 31.05, 31.06, 861.04, 861.42; 204/424, 425, 426; 436/136

(56) References Cited

U.S. PATENT DOCUMENTS

| | | | |
|---|---|---|---|
| 3,881,351 A | | 5/1975 | Prachar |
| 5,312,761 A | * | 5/1994 | Suzuki et al. ................ 436/136 |
| 6,010,615 A | | 1/2000 | Kato et al. |
| 6,033,459 A | * | 3/2000 | Hase .............................. 95/82 |
| 6,205,843 B1 | * | 3/2001 | Tanaka et al. ............. 73/31.06 |
| 6,274,016 B1 | * | 8/2001 | Hasei et al. ................ 204/424 |
| 6,338,783 B1 | * | 1/2002 | Inoue et al. ................ 204/425 |
| 6,372,120 B1 | | 4/2002 | Rössler et al. |
| 6,490,915 B2 | | 12/2002 | Yamada et al. |

FOREIGN PATENT DOCUMENTS

JP        2001-194202 A       7/2001

* cited by examiner

*Primary Examiner*—John Barlow
*Assistant Examiner*—John Le
(74) *Attorney, Agent, or Firm*—Foley & Lardner LLP

(57) ABSTRACT

A gas flow measuring device and gas flow measuring method are disclosed wherein specific gas component of measuring object gas or target gas composed of gas different from the specific gas component are added to or extracted from the measuring object gas, and concentrations C1 and C2 of the specific gas component before and after the target gas is added to or extracted. A detector (111, 121) is provided to calculate the flow rate Q1 in response to the detected concentrations C1, C2 or to detect the flow rate Q1 of the measuring object gas, and the flow rate Q3 of added or extracted target gas is detected in response to the flow rate Q1 and the concentrations C1, C2 which are detected.

32 Claims, 12 Drawing Sheets

GAS FLOW RATE MEASURING DEVICE AND GAS FLOW RATE MEASURING METHOD

BACKGROUND OF THE INVENTION

The present invention relates to a gas flow rate measuring device and a gas flow rate measuring method for measuring mass flow rate of measuring object gas.

A gas flow rate measuring device, that is available to be adopted as an air flow meter of an automotive engine, is known in the art as disclosed in a Japanese Application Laid-Open No. 2001-194202. The gas flow rate measuring device has a heater located at a center of a sensor element to heat temperature measuring resistors, disposed both the upstream and the downstream of the heater, to allow the flow rate of measuring object gas to be detected as mass flow rate passing per unit time based on a difference between resistance values detected during flow of measuring object gas over the sensor element.

Thus, if no variation takes place in composition of measuring object gas with a change with the passage of time, such as when measuring object gas prevails in an intake manifold of an automotive engine, the flow rate of measuring object gas can be accurately measured with such a thermal type flow sensor.

SUMMARY OF THE INVENTION

However, such a thermal type flow sensor encounters the following issue. That is, variation in the resistance value caused in the measuring resistor depends upon not only the flow rate of measuring object gas but also composition of the measuring resistor. This is due to the fact that a heat conductive rate of measuring object gas varies depending upon variation in the composition. Thus, if variation takes place in composition of measuring object gas, an erroneous difference occurs in measured results due to varied components. In particular, when measuring the flow rate of fuel gas in a fuel cell system, the measuring object gas contains a high concentration of steam with the concentration being liable to vary in a large extent, resulting in a difficulty of expecting an adequate accuracy.

Therefore, the present invention has an object to provide a gas flow rate measuring device and a gas flow rate measuring method which, even if variation takes place in composition of measuring object gas, enables accurate measurement of the flow rate of measuring object gas and, further, enables measurement of even the flow rate of specific gas contained in measuring object gas.

To achieve this object, a first aspect of the present invention is a gas flow measuring device comprising a gas component adjustor adding target gas, composed of specific gas component contained in measuring object gas or gas differing from the specific gas component to the measuring object gas, or extracting the target gas from the measuring object gas, a first gas concentration detector detecting a concentration of the specific gas component of the measuring object gas prevailing upstream of the gas component adjustor or setting the concentration at a predetermined level, a second gas concentration detector detecting a concentration of the specific gas component of the measuring object gas prevailing downstream of the gas component adjustor, and a gas flow rate calculator calculating at least one of the flow rate of the measuring object gas and the flow rate of the specific gas component on the basis of the concentration of the specific gas component that is detected or set by the first gas concentration detector and the concentration of the specific gas component detected by the second gas concentration detector, and the amount of the target gas added to or extracted from the measuring object gas by the gas component adjustor.

A second aspect of the present invention is a gas flow measuring device comprising a gas component adjustor adding target gas composed of specific gas component contained in measuring object gas or gas differing from the specific gas component to the measuring object gas, or extracting the target gas from the measuring object gas, a first gas concentration detector detecting a concentration of the specific gas component of the measuring object gas prevailing upstream of the gas component adjustor or setting the concentration at a predetermined level, a second gas concentration detector detecting a concentration of the specific gas component of the measuring object gas prevailing downstream of the gas component adjustor, a flow detector detecting the flow rates of the measuring object gas and the specific gas component before the target gas is added to or extracted from the measuring object gas or after the target gas is added to or extracted from the measuring object gas by the gas component adjustor, and a gas flow rate calculator calculating the amount of the target gas, added to or extracted from the measuring object gas by the gas component adjustor, on the basis of the concentration of the specific gas component, that is detected or set by the first gas concentration detector, and the concentration of the specific gas component detected by the second gas concentration detector, and the flow rate of the measuring object gas or the flow rate of the specific gas component detected by the flow detector.

A third aspect of the present invention is a method of measuring object gas flow, the method comprising adding target gas composed of specific gas component contained in measuring object gas or gas differing from the specific gas component to the measuring object gas, or extracting the target gas from the measuring object gas, detecting a concentration of the specific gas component before the target gas is added to or extracted from the measuring object gas and detecting the concentration of the specific gas component of the measuring object gas prevailing downstream thereof after the target gas has been added to or extracted from the measuring object gas, and calculating at least one of the flow rate of the measuring object gas and the flow rate of the specific gas component on the basis of the detected concentrations of the specific gas component and the amount of the target gas added to or extracted from the measuring object gas.

A fourth aspect of the present invention is a method of measuring object gas flow, the method comprising adding specific gas contained in measuring object gas or target gas composed of gas differing from the specific gas to the measuring object gas, or extracting the target gas from the measuring object gas, detecting a concentration of the specific gas component before the target gas is added to or extracted from the measuring object gas and detecting the concentration of the specific gas component of the measuring object gas prevailing downstream thereof after the target gas has been added to or extracted from the measuring object gas, detecting the flow rates of the measuring object gas or the specific gas component before the target gas is added to or extracted from the measuring object gas or after the target gas has been added to or extracted from the measuring object gas, and calculating the amount of the target gas, added to or extracted from the measuring object gas, on the basis of the detected concentrations of the specific gas component and the flow rate of the measuring object gas or the flow rate of the specific gas component.

DETAILED DESCRIPTION OF THE PREFERRED EMBODIMENTS

Hereinafter, embodiments of the present invention are described with reference to the drawings.

First, a measurement principle of the flow rate according to the present invention is described with reference to FIGS. 1A, 1B.

Figure 1A:
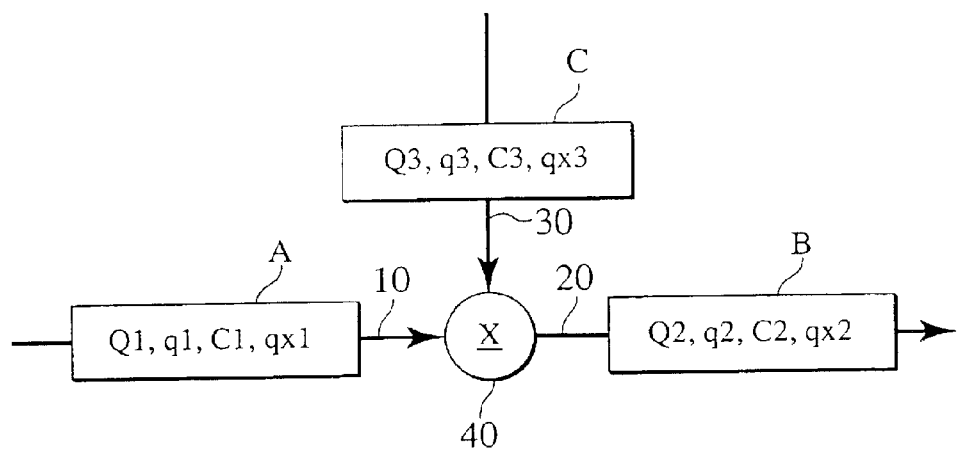
FIGS. 1A and 1B are an illustrative view of a measurement principle of the flow rate according to the present invention.
Figure 1B:
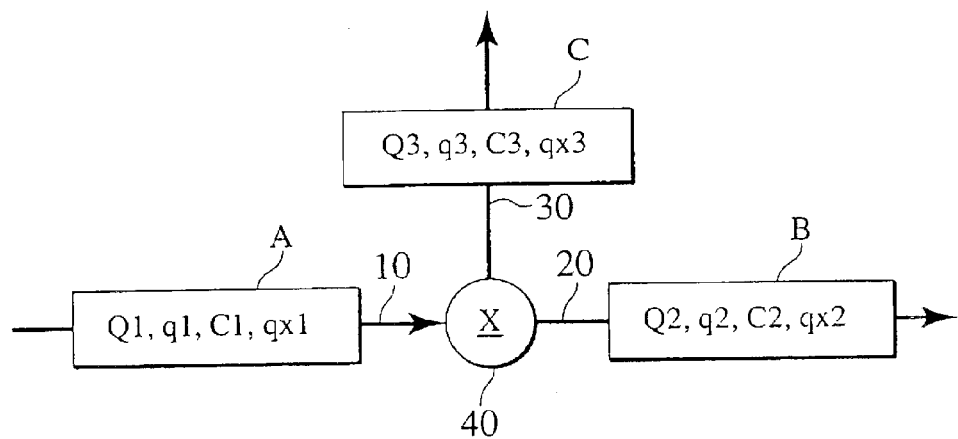

FIG. 1A shows a case where target gas is added to measuring object gas when measuring the flow rate thereof, and FIG. 1B shows a case where target gas is extracted from measuring object gas. Gas to be added to or extracted from measuring object gas as target gas may include specific gas component of measuring object gas, whose concentration is an object to be detected, or other gas (involving gas component (involving gas component (hereinafter, referred to as "composition gas component") that forms measuring object gas).

Passages 10, 20 through which measuring object gas flows, with another passage 30 being connected to a junction between the passages 10, 20. The passage 30 serves as a path to allow flow of target gas. Located at the junction between the passages 10, 20 and the passage 30 is a gas component adjustor 40. Suffixes on symbols Q, q, C, and qx indicate the associated passages 10 to 30. The symbols Q1, q1, C1, and qx1 designate status quantities of measuring object gas A, prevailing upstream of the gas component adjustor 40, involving the flow rate of measuring object gas, the flow rate of specific gas component, the concentration of specific gas component and the flow rate of composition gas component other than specific gas component. Likewise, the symbols Q2, q2, C2 and q2 designate status quantities of measuring object gas B, prevailing downstream of the gas component adjustor 40, involving the flow rate of measuring object gas, the flow rate of specific gas component, the concentration of specific gas component and the flow rate of composition gas component other than specific gas component. The symbols Q3, q3, C3 and q3 designate status quantities of measuring object gas C, flowing through the passage 30, involving the total flow rate, the flow rate of specific gas component, the concentration of specific gas component and the flow rate of gas other than specific gas component.

A first case is referred to and described in connection with an exemplary case where, as target gas, specific gas component of measuring object gas is added.

In FIG. 1A, the status quantities of measuring object gas before and after target gas is added is described as $$C1=q1/Q1, \quad (1.1)$$

$$C2=q2/Q2=(q1+q3)/(Q1+q3). \quad (1.2)$$

Elimination of Q1 from Eqs. (1. 1) and (1. 2) leads to $$q1=q3 \times C1 \times (C2-1)/(C1-C2). \quad (1.3)$$

Eq. (1. 3) shows that if it is possible to specify the concentrations C1, C2 of specific gas components, prevailing upstream and downstream of the gas component adjustor 40, and the flow rate q3 of specific gas component as target gas, the flow rate q1 of specific gas component and the flow rate Q1 (=q1/C1) of measuring object gas can be calculated.

Transformation of Eq. (1. 3) gives $$q3=q1 \times (C1-C2)/\{C1 \times (C2-1)\}. \quad (1.4)$$

Eq. (1. 4) shows that if it is possible to specify the concentrations C1, C2 of specific gas components and the flow rate q1 of specific gas component, the flow rate q3 of specific gas component as target gas and the flow rate Q2 (=Q1+q3) of measuring object gas after target gas has been added can be calculated.

A second case is referred to and described in connection with an exemplary case where gas other than specific gas component is added as target gas.

In FIG. 1A, the status quantities of measuring object gas before and after target gas is added is described as $$C1 = q1/Q1, \quad (2.1)$$

$$C2 = q2/Q2 = q1/(Q1+qx3). \quad (2.2)$$

Elimination of Eqs. (2. 1) and (2. 2) leads to $$q1 = qx3 \times C1 \times C2/(C1-C2). \quad (2.3)$$

Eq. (2. 3) shows that if it is possible to specify the concentrations C1, C2 of specific gas components and the flow rate qx3 of gas other than specific gas component, the flow rate q1 of specific gas component and the flow rate Q1 (=q1/C1) of measuring object gas can be calculated.

Transformation of Eq. (2. 3) gives $$qx3 = q1 \times (C1-C2)/(C1 \times C2). \quad (2.4)$$

Eq. (2. 4) shows that if it is possible to specify the concentrations C1, C2 of specific gas components and the flow rate q1 of specific gas component, the flow rate qx3 of target gas and the flow rate Q2 (=Q1+qx3) of measuring object gas after target gas has been added can be calculated.

A third case is referred to and described in connection with an exemplary case where specific gas component is extracted as target gas.

In FIG. 1B, the status quantities of measuring object gas before and after target gas is extracted is described as $$C1 = q1/Q1, \quad (3.1)$$

$$C2 = q2/Q2 = (q1-q3)/(Q1-q3). \quad (3.2)$$

Elimination of Q1 from Eqs. (3. 1) and (3. 2) gives $$q1 = q3 \times C1 \times (1-C2)/(C1-C2). \quad (3.3)$$

Eq. (3. 3) shows that if it is possible to specify the concentrations C1, C2 of specific gas components and the flow rate q3 of specific gas component serving as target gas, the flow rate q1 of specific gas component and the flow rate Q1 (=q1/C1) of measuring object gas can be calculated.

Transformation of Eq. (3. 3) leads to $$q3 = q1 \times (C2-C1)/\{C1 \times (C2-1)\}. \quad (3.4)$$

Eq. (3. 4) shows that if it is possible to specify the concentrations C1, C2 of specific gas components and the flow rate q1 of specific gas component, the flow rate q3 of specific gas component serving as target gas and the flow rate Q2(=Q1-q3) of measuring object gas after target gas has been extracted can be calculated.

A fourth case is referred to and described in connection with an exemplary case where gas other than specific gas component is extracted as target gas.

In FIG. 1B, the status quantities of measuring object gas before and after target gas is extracted is described as $$C1 = q1/Q1, \quad (4.1)$$

$$C2 = q2/Q2 = q1/(Q1-qx3). \quad (4.2)$$

Elimination of Q1 from Eqs. (4. 1) and (4. 2) gives $$q1 = qx3 \times C1 \times C2/(C2-C1). \quad (4.3)$$

Eq. (4. 3) shows that if it is possible to specify the concentrations C1, C2 of specific gas components and the flow rate qx3 of target gas, the flow rate q1 of specific gas component and the flow rate Q1 (=q1/C1) of measuring object gas can be calculated.

Transformation of Eq. (4. 3) leads to $$qx3 = q1 \times (C2-C1)/(C1 \times C2). \quad (4.4)$$

Eq. (4. 4) shows that if it is possible to specify the concentrations C1, C2 of specific gas components and the flow rate q1 of specific gas component, the flow rate qx3 of target gas and the flow rate Q2 (=Q1-qx3) of measuring object gas after target gas has been extracted can be calculated.

The above exemplary cases have been described in connection with attempts wherein only target gas is added or extracted using the gas component adjustor 40. The present invention is not limited to such attempts and may be applied to various cases where, under a condition wherein the concentration of target gas prevailing at least in the passage 30 is revealed, gas composed of at least two kinds of gas molecules involving target gas is added to gas. However, detection of the concentrations C1, C2 of measuring object gas upstream and downstream of the gas component adjustor 40 should not be directly affected with gas to be added to measuring object gas. When adding gas, that is different from specific gas component, as target gas, target gas may be preferably selected from gas components in consideration of chemical properties thereof with respect to measuring object gas and may be selected from gas that is hard to react with measuring object gas and has an inactive property with respect to measuring object gas. It may of course be possible for target gas to be selected from generally called inactive gases, such as nitrogen gas, helium gas or steam. In addition to these gas components, in a case where measuring object gas is steam, target gas may be selected from so-called inactive gases such as oxygen gas or hydrogen gas.

Hereinafter, an embodiment of the present invention is described in detail.

Figure 2:
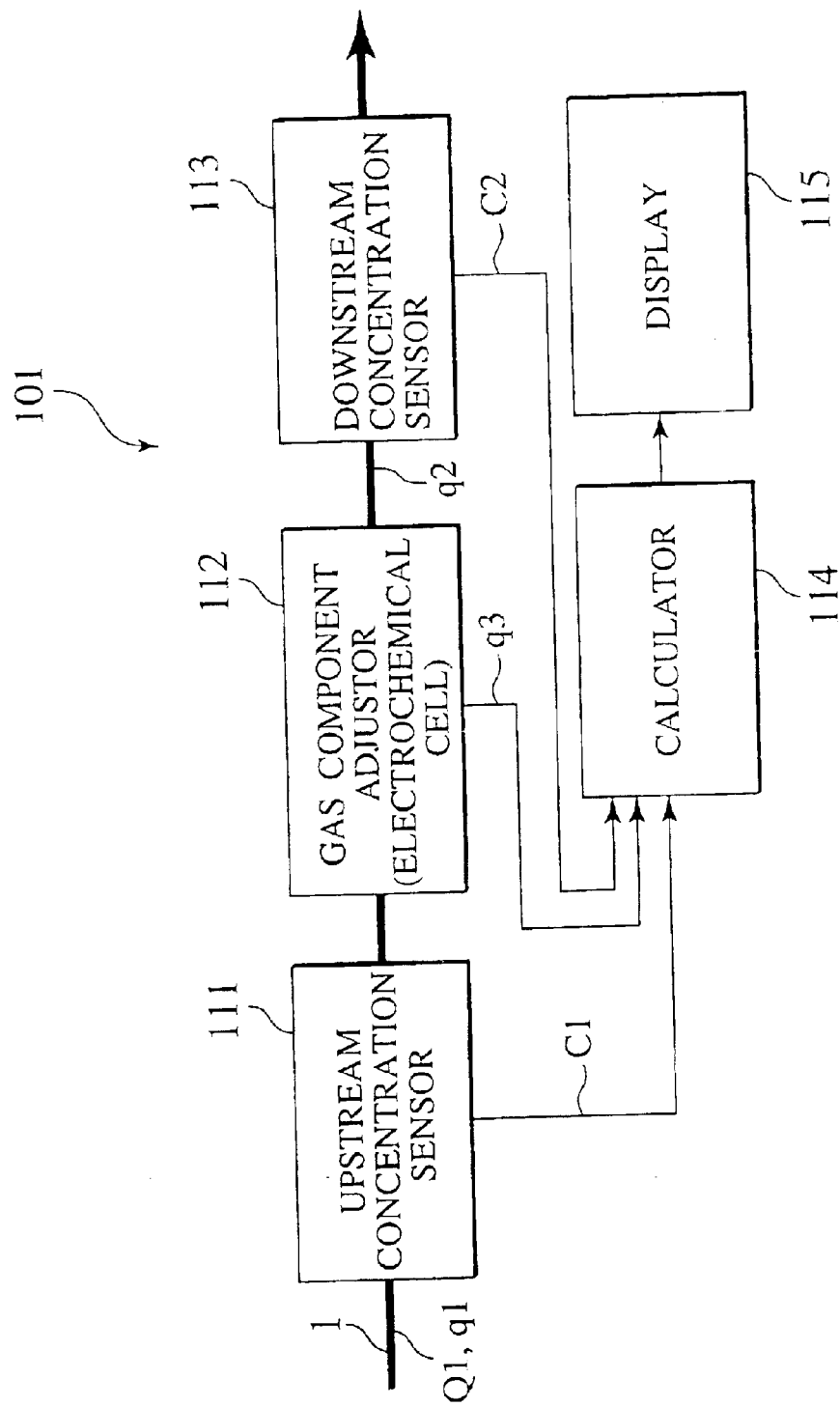
FIG. 2 is a schematic view of a gas flow rate measuring device of a first embodiment according to the present invention.

FIG. 2 is a schematic view of a gas flow measuring device 101 of a first embodiment according to the present invention.

In FIG. 2, the gas flow measuring device 101 has a measuring object gas flow passage 1, serving as a main conduit to allow measuring object gas to flow, which incorporates therein an upstream concentration sensor 111, serving as a first gas concentration detector, a gas component adjustor 112, and a downstream concentration sensor 113, serving as a second gas concentration detector, which are disposed in sequence from the upstream side in a direction of gas flow. In the presently filed embodiment, air is adopted as measuring object gas, and oxygen gas is adopted as specific gas component. Also, the gas component adjustor 112 is configured to include an electrochemical cell constructed of an oxygen ion conductive electrolyte mold body, a pair of electrodes between which the electrolyte layer is sandwiched, and an electric power supply or an electrical load connected to these electrodes.

The gas flow measuring device 101 of the presently filed embodiment operates as follows. The upstream concentration sensor 111 detects the concentration C1 of oxygen gas that forms the specific gas component of air, with a concentration detection signal c1 being outputted to a calculator 114. The gas component adjustor 112 selectively extracts oxygen gas from air flowing through the measuring object gas flow passage 1 due to pumping action of the electrochemical cell, with oxygen gas being delivered to a space outside of the passage 1. The amount q3 of extracted oxygen is expressed in a molar flow rate [mol/sec] representative of the number of oxygen molecules extracted per unit hour. The downstream concentration sensor 113 detects the concentration C2 of oxygen gas remaining in air after extraction of oxygen, with a concentration detection signal c2 being outputted to the calculator 114. The calculator 114 calculates the respective flow rates $Q1$, $q1$ [mol/sec] of air, before it enters the present device, and oxygen gas contained therein on the basis of the oxygen concentrations $C1$, $C2$ and the amount $q3$ of extracted oxygen, with resulting information ($Q1$, $q1$) being outputted to a display unit 115.

Here, if it is approximated that gas components composing air flow at the same flow speed, the oxygen concentration $C1$ can be treated as the ratio of the flow rate $q1$ of oxygen gas in terms of the flow rate $Q1$ of whole air. The calculator 114 responds to the flow rates $Q1$, $q1$ of air and oxygen gas and calculates the flow rate of oxygen gas using Eq. (3. 3) as:

$$q1 = C1 \times q3 \times (1-C2)/(C1-C2). \tag{5}$$

From Eqs. (5) and (3. 1), the flow rate of air is calculated as:

$$Q1 = q3 \times (1-C2)/(C1-C2). \tag{6}$$

However, in the above calculation process using Eqs. (3. 1), (3. 2), it is supposed that the flow rate of oxygen gas contained in air after extraction of oxygen is $q2$ [mol/sec].

Since the amount $q3$ of oxygen extracted by the gas component adjustor 112 is expressed in the molar flow rate, the flow rates $Q1$, $q1$ of air and oxygen gas calculated in Eqs. (6), (5) are also expressed in the molar flow rate. Consequently, multiplying calculated flow rates $Q1$, $q1$ by molecular weights of air or oxygen enables the flow rate to be converted into mass flow rate [g/sec]. From the flow rate $q1$ [mol/sec] of oxygen gas, mass flow rate of oxygen 32 is $q1 \times 32$ [g/sec]. Also, it is possible to convert the flow rate $q1$ of oxygen gas into dry air 28.8.

Here, with Eqs. (5), (6), when the oxygen concentrations $C1$, $C2$ equal one another, denominators become zero. Since such a situation takes place where no flow occurs, or even when flow occurs, flow is minimal, it is possible to comply with such a situation by preliminarily determining a limit from measuring accuracies of $C1$, $C2$.

As noted above, the first embodiment has been explained with reference to an exemplary case where oxygen gas serving as specific gas component is extracted from air, serving as measuring object gas, using the gas component adjustor 112. However, target gas may not necessarily need to be specific gas component but may be gas other than specific gas component. As electrolyte, it may also be possible to use the hydrogen ion conductive electrolyte mold body or a steam separation film. Forming the gas component adjustor 112 with the hydrogen ion conductive electrolyte mold body enables hydrogen gas to be extracted from measuring object gas and, further, providing hydrogen concentration sensors as the first and second gas concentration detectors 111, 113 enables the flow rate $q1$ of hydrogen gas to be calculated from Eq. (5). Further, forming the gas component adjustor 112 with a steam permeable film enables steam to be extracted from measuring object gas. Also, extraction of steam may be possibly achieved by using a condenser. When extracting gas other than specific gas component, the flow rate $q1$ of specific gas component can be calculated from Eq. (4. 3), and the flow rate $Q1$ of measuring object gas can be calculated from the following equation:

$$Q1 = q \times 3 \times C2/(C2-C1). \tag{7}$$

The gas flow measuring device of the presently filed embodiment may be configured such that a branch conduit is placed in parallel with the measuring object gas flow passage serving as the main conduit whereupon a portion of measuring object gas in the main conduit is introduced into the branch conduit to allow the flow rate of diverted gas components to be measured whereby the flow rate of diverted gas components is converted to enable calculation of the flow rates as a whole.

Figure 3:
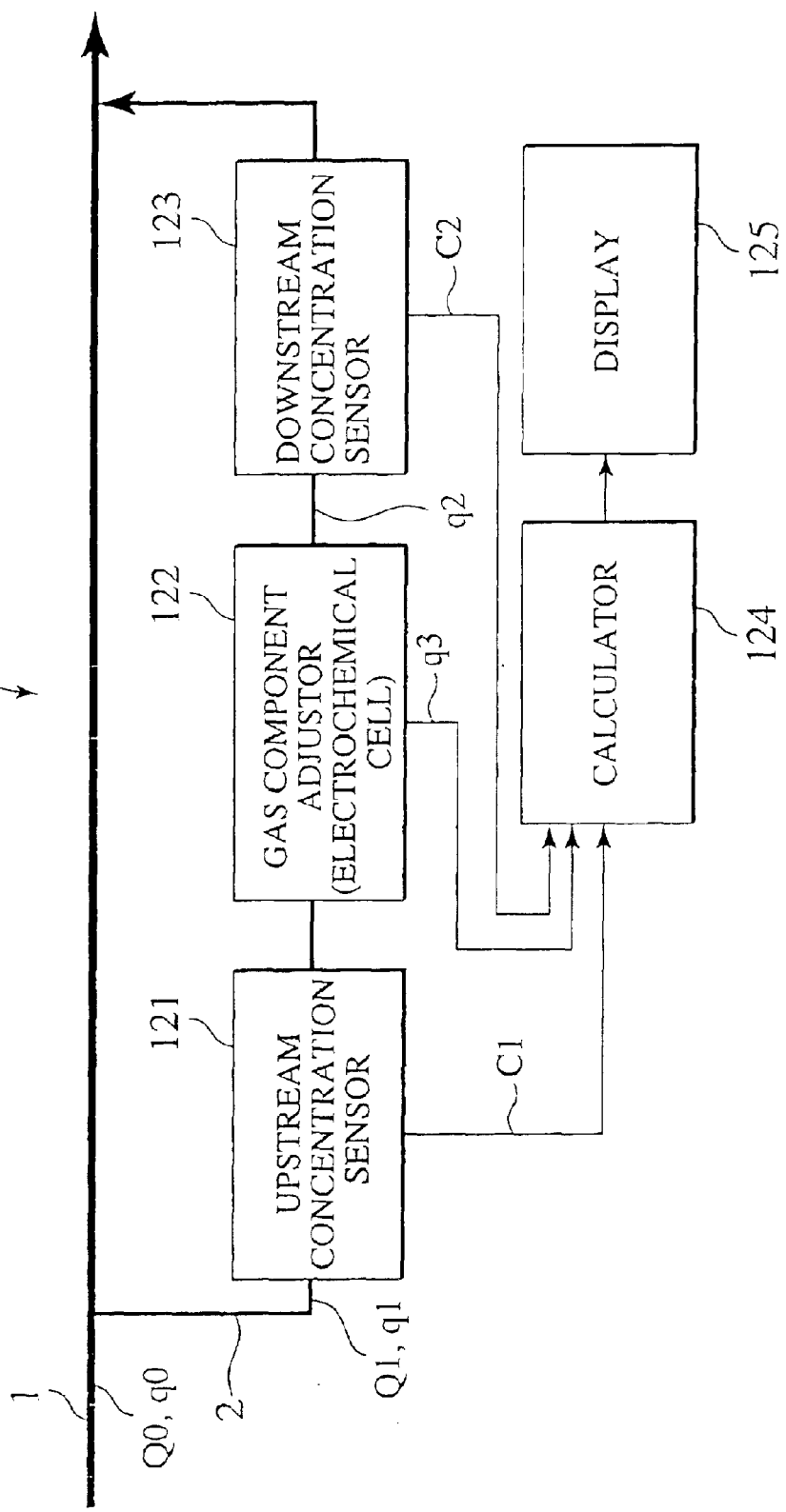
FIG. 3 is a schematic view of a gas flow rate measuring device of a second embodiment according to the present invention.

FIG. 3 is a schematic view of a gas flow measuring device 102A, formed in such a structure, of a second embodiment of the present invention.

The gas flow measuring device 102A is comprised of the measuring object gas flow passage 1, serving as a main conduit, and the second measuring object gas flow passage 2, serving as a branch conduit, which is diverged from the measuring object gas flow passage 1 at a diverging point to allow a portion of measuring object gas to be supplied into the upstream concentration sensor 121 and which is jointed to the main conduit 1 at a downstream side of the diverging point. The upstream concentration sensor 121, the gas component adjustor 122 and the downstream concentration sensor 123 are disposed in the branch conduit 2. The calculation device 124 calculates the flow rates $Q1$, $q1$ of air and oxygen gas in the branch conduit 2 using Eqs. (5), (6). The calculation device 124 stores therein a coefficient to allow the flow rates $Q1$, $q1$ of diverted gas components to be converted into the flow rates $Q0$ and $q0$ of the main conduit 1. The coefficient is preliminarily determined based on a ratio of flow sectional areas between the main conduit 1 and the branch conduit 2.

Figure 4:
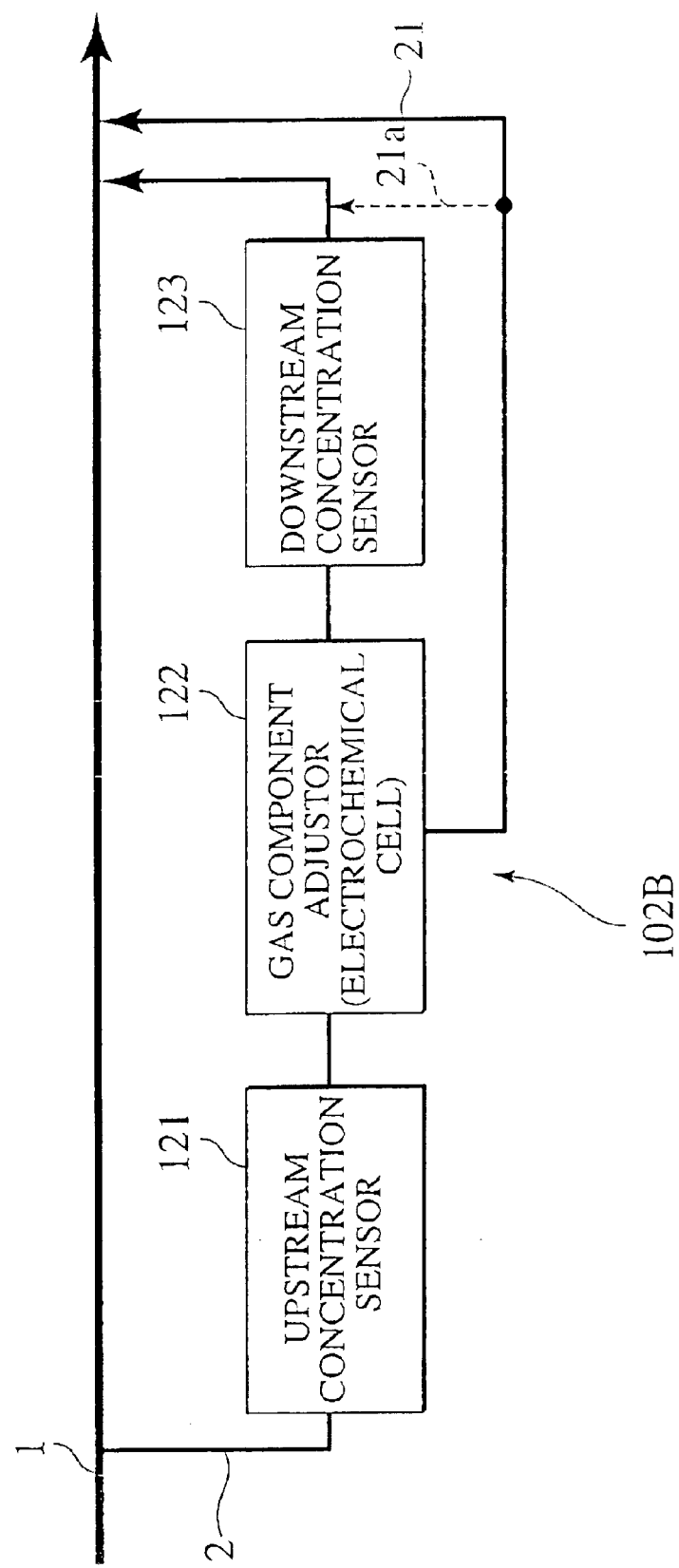
FIG. 4 is a schematic view of the gas flow rate measuring device equipped with a circulator.

As described above, when extracting target gas from measuring object gas using the gas component adjustors 112, 122, a circulator may be provided to circulate extracted target gas into measuring object gas. FIG. 4 shows a structure to achieve such a purpose. The gas flow measuring device 102B of FIG. 4 is configured such that the measuring object gas flow passage 1, serving as the main conduit, and a return conduit 21, serving as a circulator, are connected to allow extracted gas component to be circulated through the return conduit 21 to the main conduit 1 at the downstream of the diverging point. Of course, target gas may be circulated to the branch conduit 2 (as at 21a in the figure) at a downstream of the downstream concentration sensor 113, that is, at an area upstream of the converging point with the main conduit 1.

Figure 5:
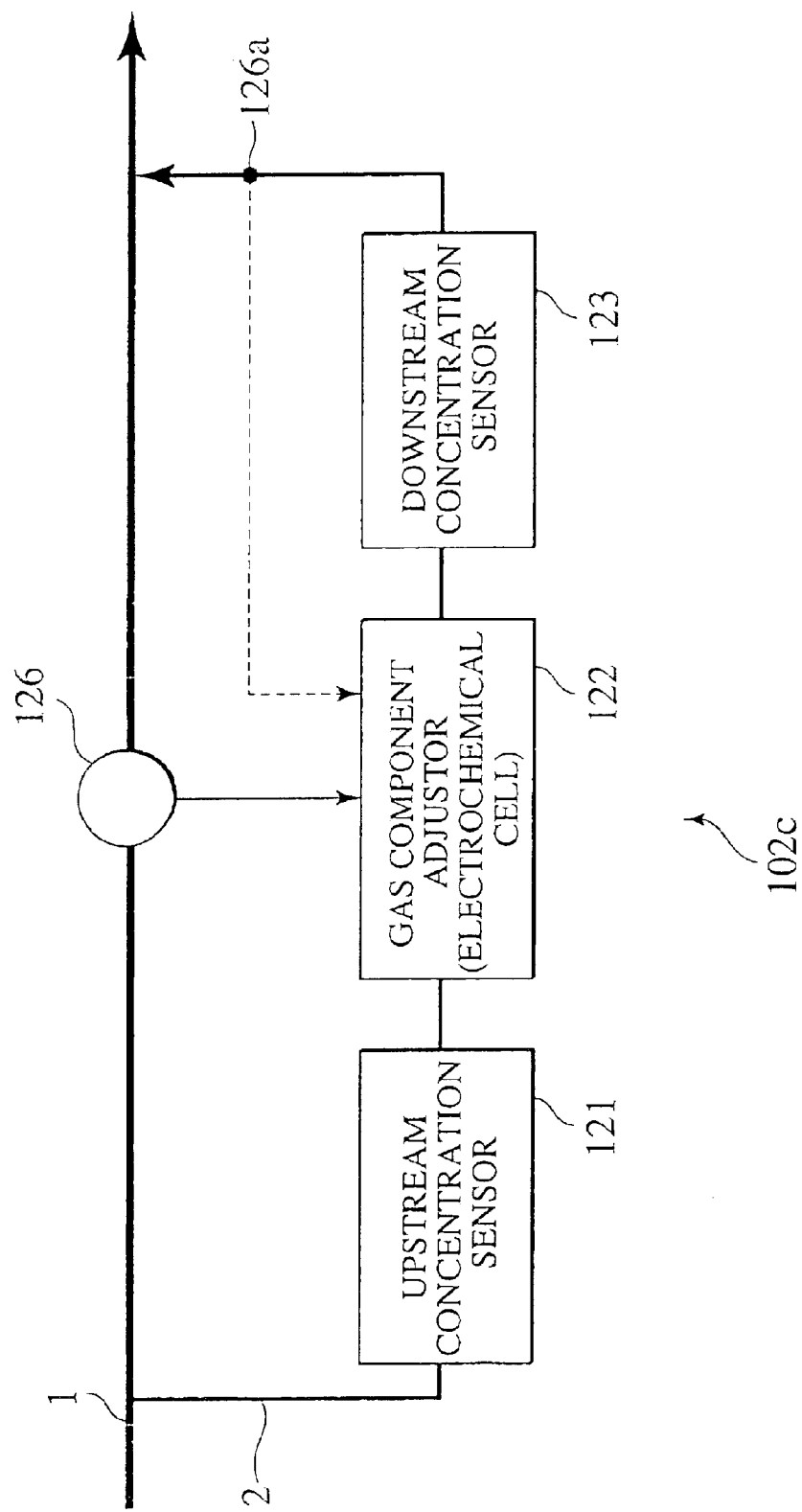
FIG. 5 is a schematic view of the gas flow rate measuring device equipped with a supplier.

Further, it may be possible for the flow rates $Q1$, $q1$ of air and oxygen gas to be calculated not only by extracting target gas but also by adding specific gas component or gas, other than specific gas component, to measuring object gas as target gas through the use of the gas component adjustors 112, 122. When adding specific gas component as target gas, the flow rates $Q1$, $q1$ can be calculated using Eq. (1. 3) wherein the sign of the amount $q3$ of extracted oxygen that is preliminarily treated is oppositely corrected. FIG. 5 shows such a structure. In the flow measuring device 102C, target gas to be added by the gas component adjustor 122 may be obtained through extraction from measuring object gas, flowing through the measuring object gas flow passage 1 serving as the main conduit, using a supplier 126. Target gas may be extracted not only from the main conduit 1 at the downstream of the diverging point but also from the branch conduit 2 at the upstream of the converging point with the main conduit 1 (as at 126a in the figure) and may be supplied to the gas component adjustor 22.

Figure 6:
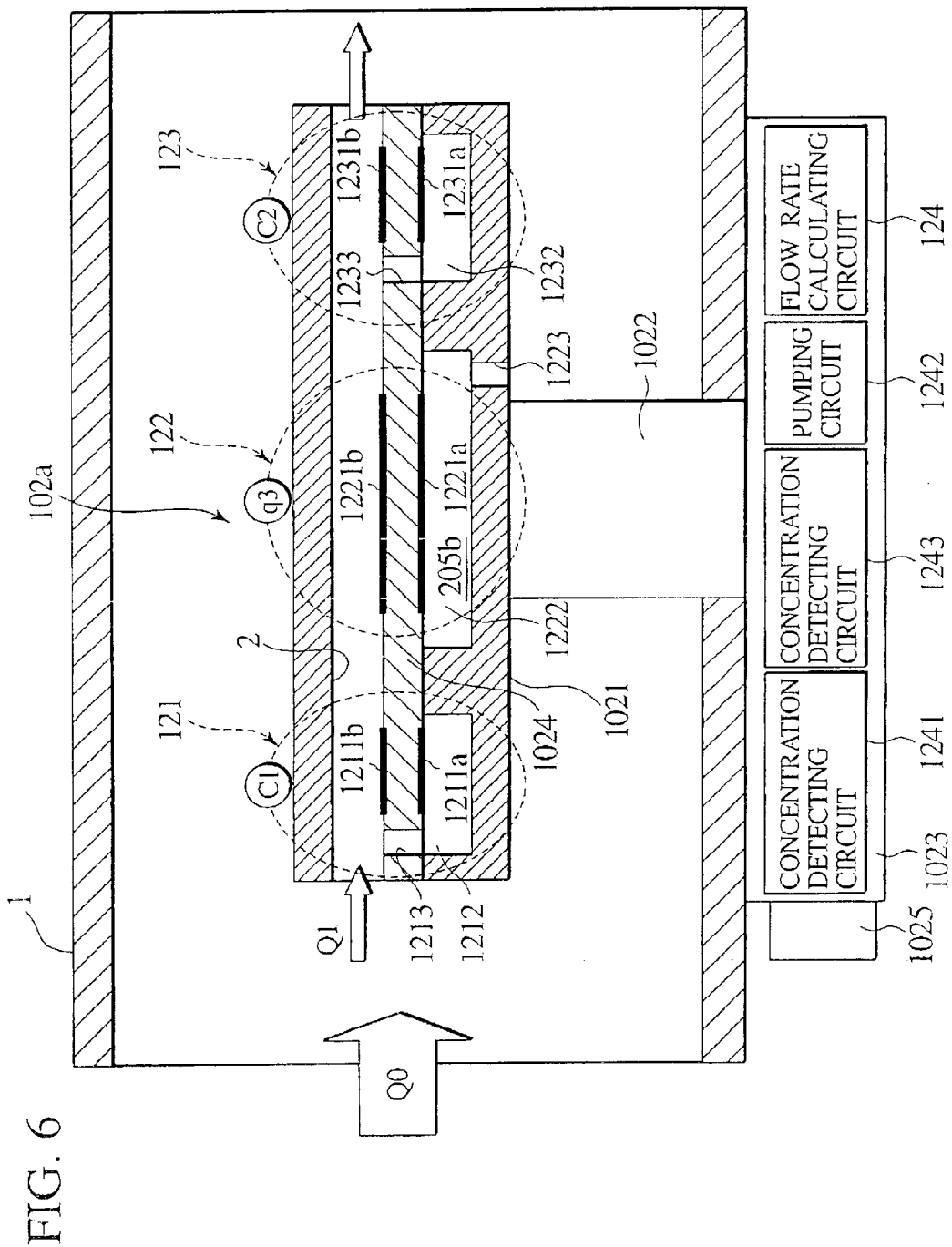
FIG. 6 is a concrete example of the gas flow rate measuring device of FIG. 3.

FIG. 6 is a structural view of a concrete example 102a of the gas flow measuring device 102A of the second embodiment.

The present device 102a includes a case 1021 in which the upstream concentration sensor 121, the gas component adjustor 122 and the downstream concentration sensor 123 are accommodated. The case 1021 is supported by a strut 1022 extending through the main conduit 1 and fixedly secured in the main conduit 1. The strut 1022 has one end coupled to the case 1021 and the other end coupled a circuit box 1023 at the outside of the main conduit 1. Also, the electrochemical cell, formed of the respective sensors 121, 123 and the gas component adjustor 122 is formed on a single oxygen ion conductive electrolyte mold body 1024 on which electrodes 1211a and 1211b of the upstream concentration sensor 121, electrodes 1221a and 1221b of the gas component adjustor 122 and electrodes 1231a and 1231b of the downstream concentration sensor 123 are formed. Formed in the case 1021 is the measuring object gas flow passage 2 which faces one side of the electrolyte 1024, with the measuring object gas flow passage 2 having fore and aft ends in communication with the main conduit 1. Accordingly, the portion of measuring object gas flowing through the main conduit 1 enters the measuring object gas flow passage 2, serving as the branch conduit, and sequentially passes across the upstream concentration sensor 121, the gas component adjustor 122 and the downstream concentration sensor 123 to be circulated to the main conduit 1.

The electrodes 1211a, 1211b of the upstream concentration sensor 121 are connected to a first concentration detecting circuit 1241 which is received in the circuit box 1023 and applied with a predetermined voltage during detection of the concentration. Formed between the case 1021 and the electrolyte 1024 so as to face the electrode 1211a is a spacing 1212 into which measuring object gas is introduced through an aperture 1213 formed to extend through the electrolyte 1024. With the electrodes 1211a, 1211b being applied with the voltage, although pumping action takes place to transfer oxygen to allow electric current to flow across the electrodes, due to limitation of inflow of measuring object gas to the spacing 1212 caused by the aperture 1213, limiting current occurs depending upon the applied voltage. The concentration detecting circuit 1241 detects the oxygen concentration C1 based on this limiting current.

Further, the downstream concentration sensor 123 has the same structure and function as those of the upstream concentration sensor 121, with the electrodes 1231a, 1231b being connected to a second concentration detecting circuit 1243. Formed between the case 1021 and the electrolyte 1024 so as to face the electrode 1211a is a spacing 1222 into which measuring object gas is introduced through an aperture 1223 formed to extend through the electrolyte 1024. With the electrodes 1221a, 1221b being applied with the voltage, since inflow of measuring object gas to the spacing 1222 is limited by the aperture 1233, limiting current occurs depending upon the applied voltage. The concentration detecting circuit 1243 detects the oxygen concentration C2 based on this limiting current.

Meanwhile, the electrodes 1221a, 1221b of the gas component adjustor 122 is connected to a pumping circuit 1242 such that, during measurement of the flow rate, the voltage across the electrodes is controlled to allow electric current flowing across these electrodes to be kept constant. Also, the spacing 1222 which the electrode 1221a faces is formed, and the spacing 1222 is in communication with the main conduit 1 via the aperture 1223 extending through the case 1021. With the electrodes 1221a, 1221b being applied with the voltage, oxygen contained in measuring object gas flowing through the measuring object gas flow passage 2 is drawn and transferred to the spacing 1222 via the electrolyte 1024. Oxygen gas transferred to the spacing 1222 in such a manner is circulated through the aperture 1223 to the main conduit 1. Here, the relation between the above-described pumping current Ip and the amount q3 of oxygen is described as $$Ip = n \times F \times J, \qquad (8)$$

where the number (four in oxygen and two in hydrogen) of electric charges is n, Faraday constant is F [C/mol] and the amount of ion transportation is J (=q3) [mol/sec].

The pumping circuit 1242 calculates the amount J of ion transportation based on the pumping current Ip using Eq. (8).

A flow rate calculation circuit 124, serving as a gas flow rate calculating means, calculates the flow rates Q1,q1 of air and oxygen on the basis of the oxygen concentrations C1, C2 and the amount J (=q3) of ion transportation detected by the concentration detection circuits 1241, 1243 and the pumping circuit 1242 and also calculates the flow rates Q1,q1 of air and oxygen on the basis of a diversion ratio of r=Q1/Q0 that is preliminarily stored.

Also, a connector 1025 delivers calculated results Q1, q1 to the display unit or other control equipments.

Further, it is possible for the pumping circuit 1242 to control the amount J (=q3) of ion transportation. This is because of the fact that, when the flow rate largely fluctuates, if the amount J of ion transportation is kept constant and determined to a value to suit for a small flow rate, the amount of oxygen gas extracted during a large flow rate becomes excessively small and no adequate difference occurs in concentration between the concentration sensors 121, 123 with resultant deterioration in resolution. Therefore, a circuit serving as a controller is incorporated in the pumping circuit 1242 to control the pumping current Ip so as to allow the amount J of ion transportation to be varied depending upon the differential concentration (C1−C2) such that a favorable differential concentration is obtained at all times.

Also, when adding target gas to measuring object gas using the gas component adjustor 122 the electrodes 1221a, 1221b are applied with the voltage in a polarity opposite to that being applied during extraction of target gas. In this case, controlling the pumping current Ip depending upon the differential concentration detected by the concentration sensors 121, 123 enables a measuring accuracy to be highly improved.

The first and second embodiments set forth above are able to have the following advantageous effects.

First, the gas flow measuring devices 101, 102 are configured so as to measure the flow rates Q1, q1 of measuring object gas and specific gas component responsive to the flow rate q3 of target gas added or extracted through the gas component adjustors 112, 122 and the concentrations C1, C2 of specific gas components detected at each of the upstream side and the downstream side of such devices 112, 122. For this reason, even in occurrence of variation in composition of measuring object gas flowing through the main conduit 1 to cause variation in thermal characteristic of measuring object gas, the flow rates Q1, q1 can be accurately detected. Also, due to an ability of detecting the concentration C1 of specific gas component using the gas concentration detecting means 111, 121 during measurement, a particularly useful advantage is resulted not only in measuring the flow rates but also in grasping such a concentration C1.

Secondly, due to abilities of the gas component adjustors 112, 122 adapted to variably control the amount J of ion transportation between the electrodes such that the amount J of ion transportation during flow at a large flow rate becomes higher than that during flow at a low flow rate, it becomes possible form the differential concentration (C1−C2) required for accurate measurement in a wide measuring range.

Thirdly, as shown in FIG. 6, due to provision of the structure wherein the electrolyte that forms the concentration sensors 121, 123, serving as the gas concentration detecting means, and the electrolyte that forms the gas component adjustor 122 are integrated, the gas flow measuring device 102a can be manufactured in a small size and light weight, resulting in reduction in cost. Also, since the concentration sensors 121, 123 can be located closer to one another, a difference in measurement times between the associated sensors can be accurately corrected, thereby enabling improvement in a measurement accuracy during fluctuation in the transitional flow rate.

Fourthly, as shown in FIGS. 3 and 6, due to an ability of the portion of measuring object gas, flowing through the main conduit 1, being compelled to flow through the gas flow measuring devices 102, 102a to allow the flow rates Q0, q0 as a whole to be measured based on the flow rate Q1, q1 of such diverged components, specific gas component can be uniformly distributed in diverged components of measuring object gas. For this reason, a concentration detection accuracy for specific gas component can be improved, providing a capability of more accurately measuring the flow rate.

Hereinafter, other structural examples of the flow measuring device according to the present invention.

Figure 7:
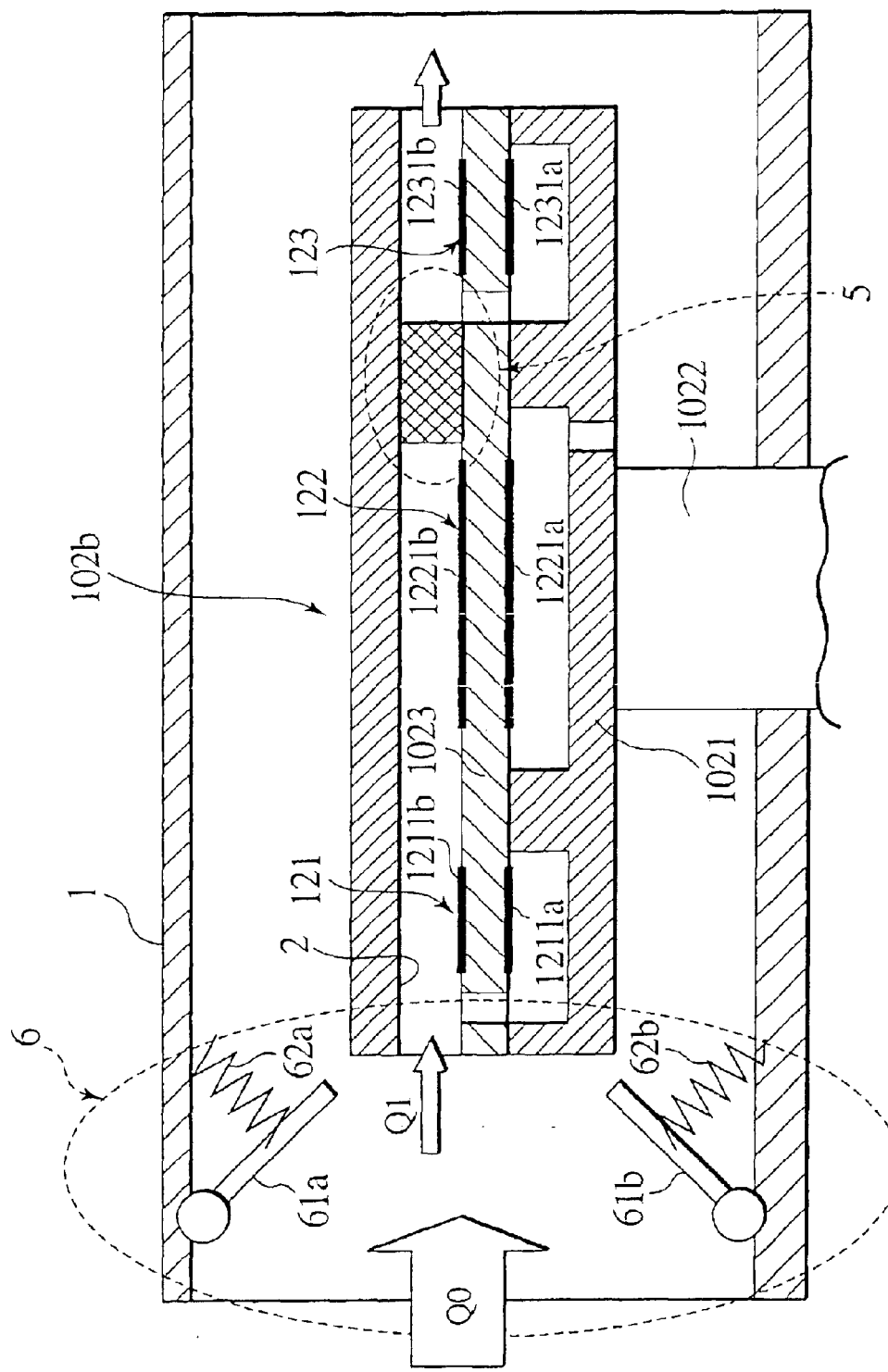
FIG. 7 is a concrete example of the gas flow rate measuring device equipped with a mixer and a variable unit.

FIG. 7 is a structural view of a second concrete example 102b of the gas flow measuring device according to the second embodiment.

The present device 102b is comprised of a mixer 5 and a variable unit 6. As the mixer 5, a porous body is adopted, and the porous body 5 is disposed in the measuring object gas flow passage 2, serving as the branch conduit, at a position between the gas component adjustor 122 and the downstream concentration sensor 123. On the other hand, the variable unit 6 is disposed in the measuring object gas flow passage 1 at an area upstream of the present device 102b. The variable unit 6 is structured as a means for reducing the flow surface area of the main conduit 1 and includes flat plates 61a, 61b rotationally pivoted on the conduit wall and springs 62a, 62b, as resilient members, which are mounted between these respective flat plates and the conduit wall.

With the mixer 5, when adding or extracting oxygen gas, serving as specific gas component, as target gas, the detection accuracy of the downstream concentration sensor 123 can be improved. Due to an ability of air, to which oxygen gas is locally added by the gas component adjustor, to be mixed, oxygen gas can be uniformly distributed at the installed position of the downstream concentration sensor. Further, by additionally providing the mixer 5, even if the gas component adjustor 122 and the downstream concentration sensor 123 is located relatively closer to one another, it is possible to obtain the concentration with the downstream concentration sensor 123 at a high reliability, resulting in a capability of miniaturization of the present device 102b.

Meanwhile, in the variable unit 6, the flat plates 51a, 61b function as valves that open or close in dependence on the flow rate Q0 of the main conduit 1 and are displaced at position balanced between a force exerted from flow and a force exerted from the springs 62a, 62b. Accordingly, during flow at the large flow rate, since the flat plates 61a, 6ab are caused to tilt and expand the flow surface area of the main conduit 1, it becomes possible to preclude flow from being exerted with excessively large resistance. During flow at the small flow rate, since the respective flat plates are raised up and increase the ratio of measuring object gas, to be supplied to the present device 102b, in terms of the whole measuring object gas, the measuring accuracy can be improved in a range of flow at the small flow rate, while enabling a measurable lower-limit flow rate to be trickled down. Also, the variable unit 6 may be disposed in the branch conduit 2 and, in such case, springs may be provided to as to allow a flow path is opened during flow at the small flow rate. The variable unit 6 may also be comprised of a variable venturi.

Figure 8:
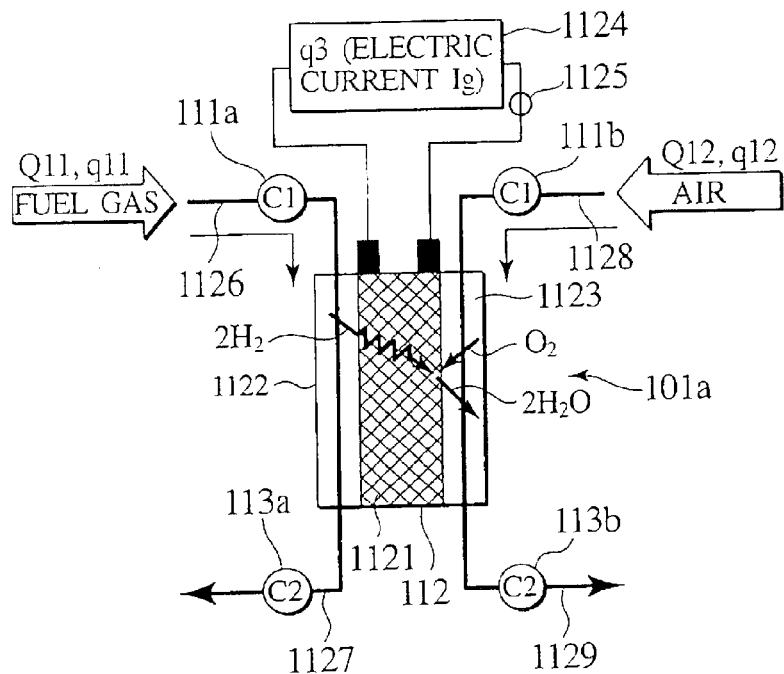
FIG. 8 is a concrete example of the gas flow rate measuring device of FIG. 2 equipped with a fuel cell as a gas component adjustor.

FIG. 8 is a structural view of a concrete example 101a of the gas flow measuring device of the first embodiment.

In the present device 101a, a fuel cell is adopted as the gas component adjustor 112. The fuel cell 112 is constructed of a hydrogen ion conductive electrolyte mold body 1121, composed of a high polymer solid electrolyte or an oxide solid electrolyte formed at both sides thereof with electrodes 1122, 1123 serving as an anode and a cathode, with the anode 1122 and the cathode 1123 being supplied with hydrogen containing gas and air, as oxygen gas, respectively. Also, an electric load 1124 is connected between the anode 1122 and the cathode 1123, to which an electric current sensor 1125 is connected for detecting electric current Ig flowing through the load 1124.

Disposed in a fuel gas supply conduit 1126 which is connected to an inlet of the anode 1122 is an upstream hydrogen concentration sensor 111a and, likewise, a downstream hydrogen concentration sensor 113a is disposed in a fuel gas outlet conduit 1127 extending from an outlet of the anode 1122. A calculation unit calculates the flow rate Q11 of fuel gas and the flow rate q11 of hydrogen gas contained in fuel gas based on Eqs. (5), (6) on the basis of hydrogen concentrations C1, C2 detected by the respective concentration sensors 111a, 113a and the amount (equivalent to the amount of ion transportation) q31 [mol/sec] of hydrogen transferred through the electrolyte 1121. Here, the amount q31 of transferred hydrogen can be derived from a univocal relationship associated with the electric current value Ig detected by the electric current sensor 1125.

Meanwhile, an upstream oxygen concentration sensor 111b is disposed in an air supply conduit 1128 which is connected to an inlet of the cathode 1123 and, likewise, a downstream oxygen concentration sensor 113b is disposed in an air outlet conduit 1129 extending from an outlet of the cathode 1123. The calculation unit calculates the flow rates Q12, q12 of air and oxygen gas on the basis of oxygen concentrations C12, C22 detected by the respective concentration sensors 111b, 113b and the amount q32 [mol/sec] of extracted oxygen substantially extracted through conversion into water. Also, the amount q32 of extracted oxygen can be derived from a univocal relationship associated with the electric current value Ig detected by the electric current sensor 1125. The respective flow rates Q12, q12 are calculated as follows.

In the cathode 1123, different from the anode 1122, water is formed accompanied by electric power generation of the fuel cell 112. The amount of water reaches a value two times the amount Q32 of extracted oxygen as expressed in a chemical equation: $2H_2+O_2 \rightarrow 2H_2O$. Consequently, a equation corresponding to the Eq. (3. 2) is represented as $$C2 = (q1 - q3)/(Q1 - q3 + 2 \times q3) \quad (3.2.2)$$
$$= (q1 - q3)/(Q1 + q3).$$

Equation corresponding to Eqs. (6), (5) is represented as $$q1 = C1 \times q3 \times (1+C2)/(C1-C2), \quad (9)$$

$$Q1 = q3 \times (1 \times C2)/(C1 \times C2), \quad (10)$$

The calculation unit calculates the flow rates Q12, q12 of air and oxygen gas based on Eqs. (9), (10).

Figure 9:
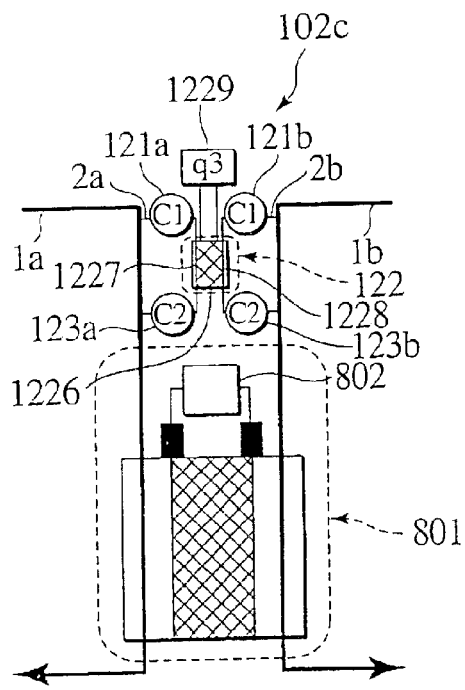
FIG. 9 is a concrete example of the gas flow rate measuring device of FIG. 3 equipped with a fuel cell as a gas component adjustor.

FIG. 9 is a structural view of a third concrete example 102c of the gas flow measuring device of the second embodiment.

In the present device 102c, as the gas component adjustor 122, a further miniaturized fuel cell is provided separately from a fuel cell 801 serving as an electric power supply of a fuel cell system. Reference numeral 802 designates an electrical load.

The present device 102c is constructed of a hydrogen ion conductive electrolyte mold body 1126, composed of a high polymer solid electrolyte, formed at both sides thereof with an anode 1227 and a cathode 1228, to which portions of hydrogen gas and oxygen gas flowing through main conduits 1a, 1b are supplied via branch conduits 2a, 2b, respectively. An upstream hydrogen concentration sensor 121a and a downstream hydrogen concentration sensor 123a are disposed in the branch conduit 2a on both sides of the anode 1227, and an upstream oxygen concentration sensor 121b and a downstream oxygen concentration sensor 123b are disposed in the branch conduit 2b on both sides of the cathode 1228. An electrical load 1229 of the flow measuring fuel cell 122 that forms a portion of a load 802 of an electric power supply fuel cell 801. The calculation unit calculates the flow rates Q110, q110 of fuel gas and hydrogen gas in a main conduit 1a and the flow rates Q120, q120 of fuel gas and hydrogen gas in a main conduit 1b based on Eqs. (5), (6), (9), and (10) on the basis of concentrations C11, C21 and C22 detected by the respective concentration sensors 121a, 123a, 121b and 123b, the electric current Ig flowing through the load 1229 and the diversion ratio r.

According to the present device 101c, providing the small size measuring fuel cell 122 separately from the electric power supply fuel cell 801 enables response to be improved to a higher level and allows a higher measuring accuracy to be maintained even during transitional operation than those of a case where the electric power supply fuel cell 112 doubles as the flow rate measuring electrochemical cell as shown in FIG. 8. Also, by locating the flow rate measuring electrochemical cell 122 at the area upstream of the electric power supply fuel cell 801, since the flow rate Q110 of fuel gas flowing through the main conduits 1a, 1b can be measured prior to a phase where fuel gas is supplied to the fuel cell 801, the fuel cell 801 can be properly controlled.

Figure 10:
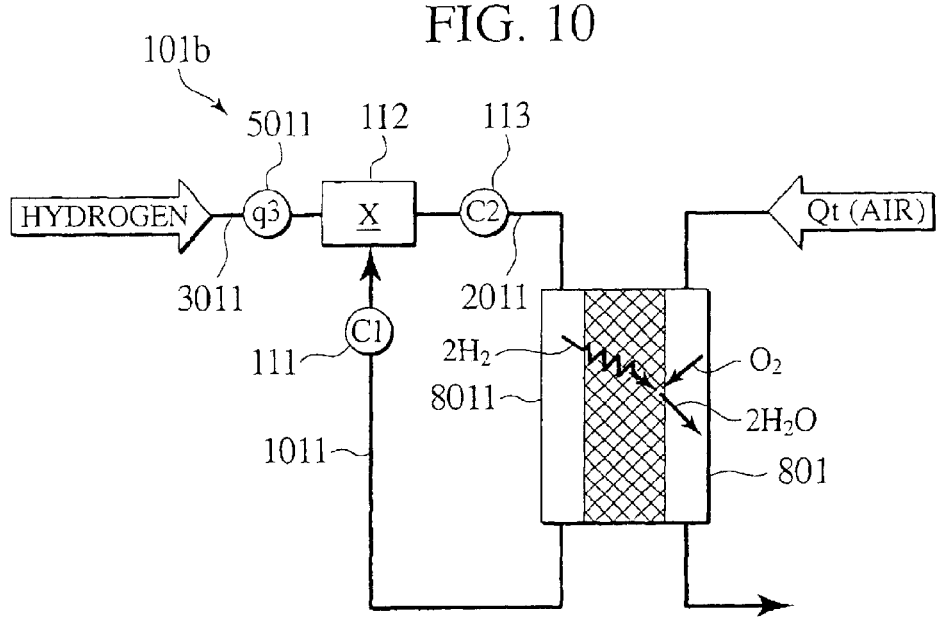
FIG. 10 is a structural view of the gas flow rate measuring device that is applied to measure the flow rate of hydrogen gas to be supplied to a fuel cell.

FIG. 10 is a structural view of a second concrete example 101b of the gas flow measuring device of the first embodiment.

In the present device 101b, fuel gas (hereinafter referred to as "circulated fuel gas") exhausted from the electric power supply fuel cell 801 of the fuel cell system and circulated to the fuel cell 801 is employed as measuring object gas, and fresh hydrogen gas to be added as supplementary component or weighting component is adopted as target gas. The present device 101b measures the flow rate q2 of hydrogen gas to be supplied to the fuel cell 801. A confluence section 112 is interposed as a gas component adjusting means between fuel gas supply conduits 3011, 2011 that interconnect a hydrogen tank, which is not shown, and the fuel cell 801. A fuel gas supply conduit 1011 extending from an outlet of an anode 8011 of the fuel cell 801 is connected to the confluence section 112, with a fuel gas exhaust conduit 1011 and the fuel gas supply conduit 2011 forming a circulation path for fuel gas. Fresh hydrogen gas is supplied from the hydrogen tank and joins circulated fuel gas in the confluence section 112 to flow into the fuel gas supply conduit 2011 at the downstream side. A zirconia oxygen sensor 111, serving as a first gas concentration detector, is disposed in the fuel gas exhaust conduit 1011, and a zirconia oxygen sensor 113, serving as a second gas concentration detector, is disposed in the fuel gas supply conduit 2011. These sensors 111, 113 detect the hydrogen concentrations C1, C2 of fuel gas. Also, a mass flow meter 5011 is disposed in the fuel gas supply conduit 3011 upstream of the confluence section 112 for detecting the flow rate q3 of hydrogen gas. Since hydrogen gas to be supplied from the hydrogen tank has dry hydrogen gas with no inclusion of other components, the mass flow meter 5011 of a general type may be employed.

The calculation unit calculates the flow rate q1 of hydrogen gas contained in circulated fuel gas flowing through the fuel gas supply conduit 1011 based on Eq. (1. 3) on the basis of the hydrogen concentrations C1, C2 detected by the zirconia oxygen sensors 111, 113 and the flow rate q3 of hydrogen gas detected by the mass flow meter 5011. Also, the calculation unit calculates the flow rate q2 of hydrogen gas to be supplied to the fuel cell 801 by adding the calculated flow rate q1 and the flow rate q3 of fresh component (q2=q1+q3).

With the present device 101b, the flow rate q1 of hydrogen gas contained in circulated fuel gas can be measured, while enabling the flow rate q2 of hydrogen gas, contained in fuel gas to which fresh hydrogen gas is added, to be measured. Since the amount of electric power generated by the fuel cell 801 depends upon the amount of hydrogen gas supplied thereto, an ability of measuring the flow rates q1, q2 in such a manner contributes to improvement in an efficiency of the fuel cell 801.

Figure 11:
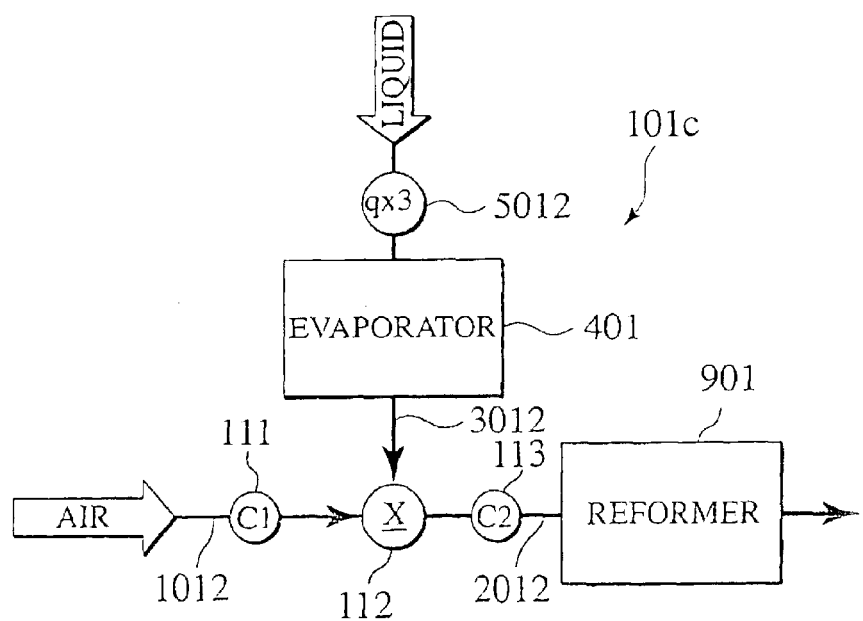
FIG. 11 is a structural view of the gas flow rate measuring device that is applied to measure the flow rate and a concentration of steam to be supplied to a fuel reformer of a fuel cell electric power generation system.

FIG. 11 is a structural view of a third concrete example 101c of the gas flow measuring device of the first embodiment.

In the present device 101b, air is adopted as measuring object gas and steam is adopted as target gas to be added to air. The present device 101c measures the flow rate qx2 and the concentration Cx2 of steam to be supplied to a fuel reformer 901 of the fuel cell system. Steam is generated by evaporating water by an evaporator 401. Steam is supplied from a water tank, which is not shown, and added to air in the confluence section 112. The confluence section 112 and the evaporator 401 form a gas component adjusting means. A zirconia oxygen sensor 111, serving as a first gas concentration detector, is disposed in an air flow passage 1012 upstream of the confluence section 112, and a zirconia oxygen sensor 113, serving as a second gas concentration detector, is disposed in a downstream air flow passage 2012. These sensors 111, 113 detect the oxygen concentrations C1, C2 in air. Also, a mass flow meter 5012 is disposed in a water supply conduit for detecting the flow rate qx3 of water to be supplied to the evaporator 401, with detected flow rate qx3 being treated as the flow rate of steam to be added to air.

The calculation unit calculates the flow rate q1 (=q2) of oxygen gas to be supplied to the reformer 901 based on Eq. (2. 3) on the basis of the oxygen concentrations C1, C2 detected by the zirconia oxygen sensors 111, 113 and the flow rate qx3 of steam detected by the mass flow meter 5012. Due to the presence of the oxygen concentration C1 of air detected by the zirconia oxygen sensor 111 at the upstream side, the calculation unit calculates the flow rate Q1 of air based on Eq. (2. 1) while calculating the flow rate qx1 of steam in the air flow passage 1012 upstream of the confluence section 112, using the following equation, on the supposition that a mixture ratio between oxygen and nitrogen in air is 1:3.77:

$$qx1 = Q1 - q1 - 3.77 \times q1. \tag{11}$$

The calculation unit further calculates the flow rate qx2 and the concentration Cx2 of steam in the air flow passage 2012 downstream of the confluence section 112 using the following Equations:

$$qx2 = qx1 + qx3, \quad (12)$$

$$Cx2 = qx2/(Q1 + qx3), \quad (13)$$

With the gas flow measuring device of the presently filed embodiment, even in a case where, like air, measuring object gas contains a plurality of composition constituents other than specific gas, no issue arises in the number of the kinds of the composition constituents whose ratio in terms of specific gas component is revealed. In the above third concrete example 101c, although nitrogen gas other than oxygen gas serving as specific gas component is contained in air as composition constituent, since the ratio (=3.77) of nitrogen gas in terms of oxygen gas is revealed, not only the flow rate of oxygen gas but also the flow rate and concentration of nitrogen gas can be measured.

Figure 12:
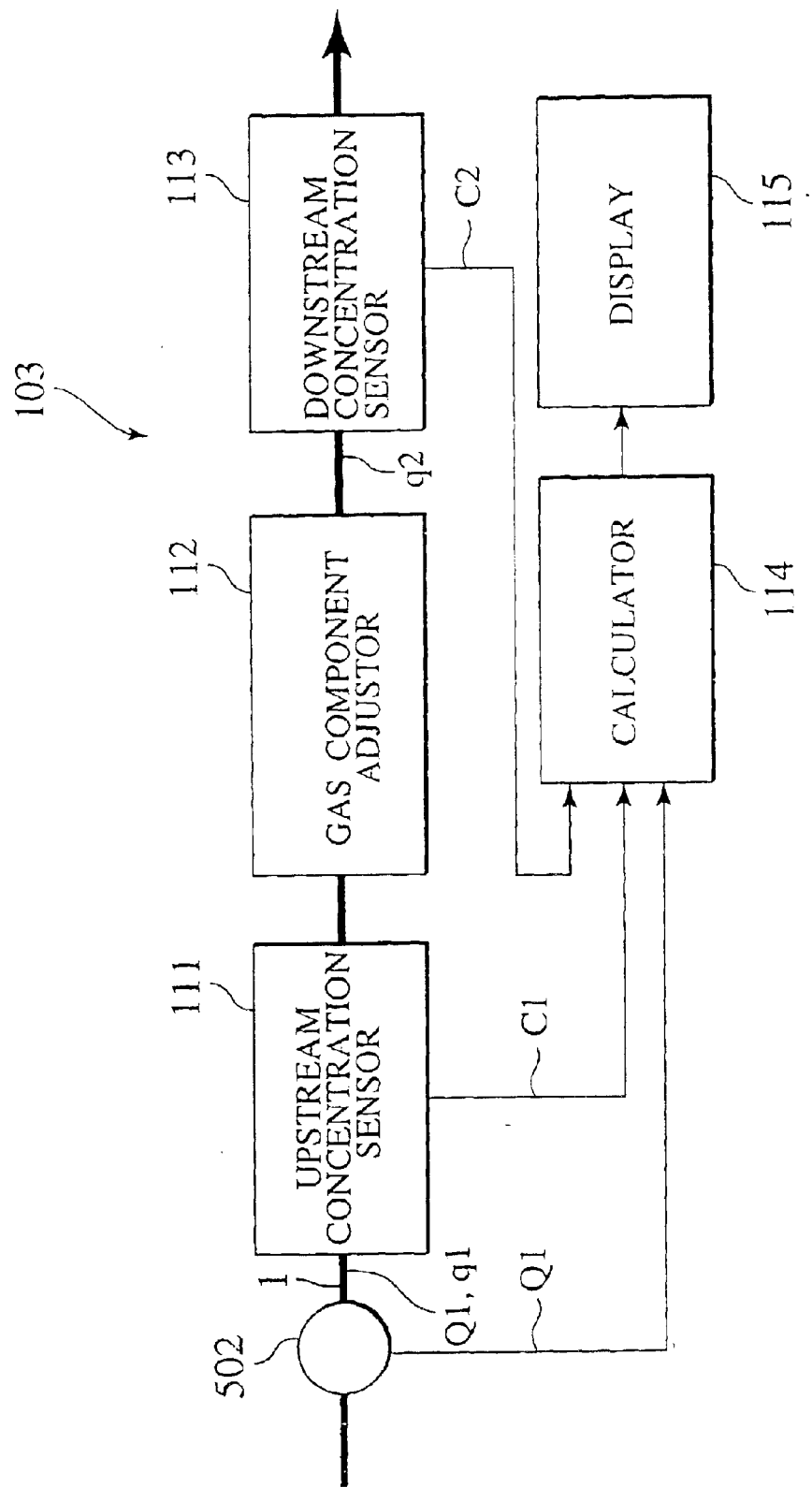
FIG. 12 is a schematic view of a gas flow rate measuring device of a third embodiment according to the present invention.

FIG. 12 is a schematic view of a gas flow measuring device 103 of a third embodiment of the present invention.

Disposed in a measuring object gas flow passage 1 serving as a main conduit to allow flow of measuring object gas sequentially from an upstream side in a flow direction are an upstream concentration sensor 111, a gas component adjustor 112 and a downstream concentration sensor serving as a second gas concentration detector. Also, a mass flow meter 502 is disposed as a flow detector in the measuring object gas flow passage upstream of the gas component adjustor 112.

The upstream concentration sensor 111 detects the concentration C1 of specific gas component contained in measuring object gas. The gas component adjustor 112 serves to add specific gas component or target gas, formed of gas different from specific gas component, to measuring object gas or extracting the same from measuring object gas. The downstream concentration sensor 113 detects the concentration C2 of specific gas in air after specific gas has been added or extracted. The mass flow meter 502 detects the flow rate Q1 of specific gas. The calculation unit 114 serving as the gas flow calculation means calculates the flow rates q3, qx3 of object based on Eqs. (1. 4), (2. 4), (3. 4) or (4.4) on the basis of the concentrations C1, C2 of specific gas detected by the respective sensors 111, 113 and the flow rate Q1 detected by the mass flow meter 502.

Figure 13:
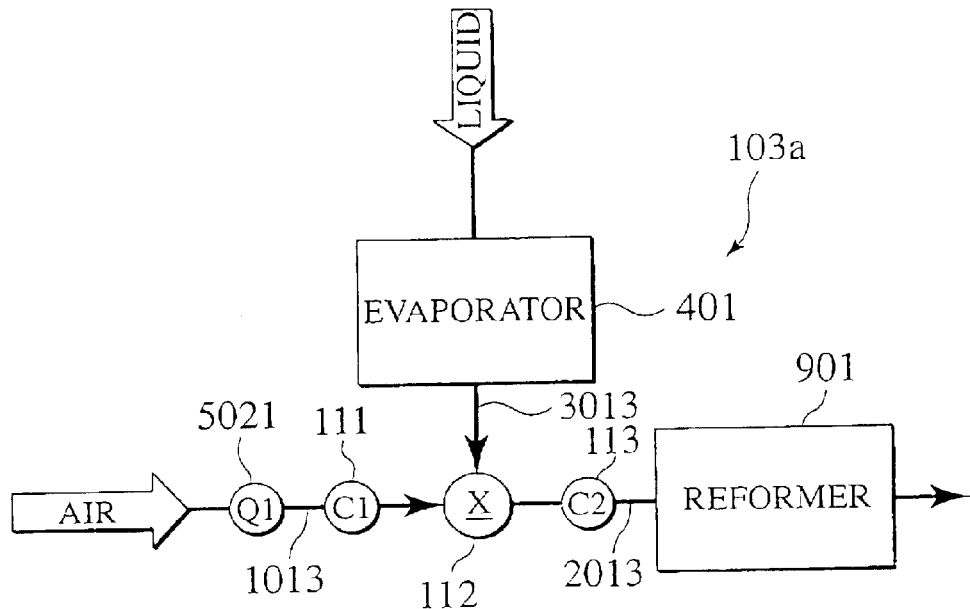
FIG. 13 is a structural view of the gas flow rate measuring device that is applied to measure the flow rate of steam to be supplied to a fuel reformer.

FIG. 13 is a structural view of a concrete example 103a of a gas flow measuring device of the third embodiment.

In the present device 103a, air is adopted as measuring object gas and steam is adopted as target gas to be added to air. The present device 103a measures the flow rate qx2 of steam to be supplied to the fuel reformer 901 of the fuel cell system. Steam is generated by evaporating water by the evaporator 401. Air flow passages 1013, 2013, each serving as a main conduit, have one end opened to atmosphere and the other end connected to the reformer 901. Steam generated by the evaporator 401 is added to air in the confluence section 112 that serves as the gas component adjustor. Connected to the air flow passages 1013, 2013 upstream of and downstream of the confluence section 112, respectively, are zirconia oxygen sensors 111, 113. These sensors 111, 113 detect the oxygen concentrations C1, C2 in air. Also, a mass flow meter 5021 is disposed in the air flow passage 1013 upstream of the confluence section 112 for detecting the flow rate Q1 of air. Since air drawn from the atmosphere is dry or even if it is wet, since the temperature is stabilized, the flow rate Q1 can be detected through the use of the mass flow meter of a general type. Also, if the moisture of air is unstable and its fluctuation can not be neglected, the detected flow rate Q1 may be corrected with the moisture that is preliminarily measured, or a moisture sensor may be disposed in the measuring object gas flow passage 1 and may be corrected with resulting detected value.

The flow rate qx2 of steam contained in air to be supplied to the reformer 901 is equal to the flow rate qx3 of steam to be added by the evaporator 401 and can be calculated in Eq. (2. 4).

Also, if air drawn from the atmosphere is dry, the upstream zirconia oxygen sensor 111 can be omitted utilizing a normal mixture ratio oxygen gas in air in a range of the value of 20.9%.

FIG. 12 is a schematic view of a gas flow measuring device 103 of a third embodiment of the present invention.

Disposed in the measuring object gas flow passage 1 serving as the main conduit to allow flow of measuring object gas sequentially from the upstream side in a flow direction are the upstream concentration sensor 111, the gas component adjustor 112 and the downstream concentration sensor 113 serving as the second gas concentration detector. Also, the mass flow meter 502 is disposed as the flow detector in the measuring object gas flow passage upstream of the gas component adjustor 112.

The upstream concentration sensor 111 detects the concentration C1 of specific gas component contained in measuring object gas. The gas component adjustor 112 serves to add specific gas component or target gas, formed of gas different from specific gas component, to measuring object gas or extracting the same from measuring object gas. The downstream concentration sensor 113 detects the concentration C2 of specific gas in air after specific gas has been added or extracted. The mass flow meter 502 detects the flow rate Q1 of specific gas. The calculation unit 114 serving as the gas flow calculation means calculates the flow rates q3, qx3 of object based on Eqs. (1. 4), (2. 4), (3. 4) or (4.4) on the basis of the concentrations C1, C2 of specific gas detected by the respective sensors 111, 113 and the flow rate Q1 detected by the mass flow meter 502.

Figure 14:
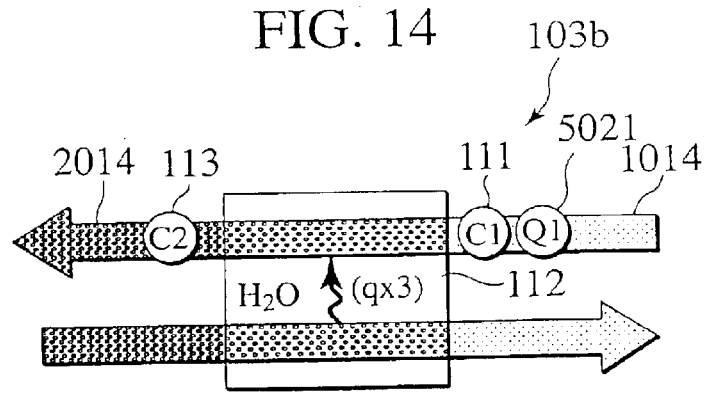
FIG. 14 is a structural view of the gas flow rate measuring device that is applied to measure the flow rate of steam to be added by a humidifier of a fuel cell electric power generation system.

FIG. 14 is a structural view of a second concrete example 103b of the gas flow measuring device of the third embodiment.

In the present device 103b, air is adopted as measuring object gas and steam is adopted as target gas to be added to air. The present device 103b measures the amount of steam, added by a humidifier 112, as the flow rate qx3, of the fuel cell system. The humidifier 112 forms a gas component adjustor. Disposed in air flow passages 1014, 2014 upstream of and downstream of the humidifier 112, respectively, are zirconia oxygen sensors 111, 113. These sensors 111, 113 detect the oxygen concentrations C1, C2 in air. Also, a mass flow meter 5021 is disposed in the air flow passage 1014 upstream of the humidifier 112 for detecting the flow rate Q1 of air.

The flow rate qx2 of steam contained in air to be supplied to the fuel cell is equal to the amount of steam to be added by the humidifier 112. Accordingly, the flow rate qx2 (=qx3) can be calculated based on Eq. (2. 4) on the basis of the oxygen concentrations C1, C2 detected by the zirconia oxygen sensors 111, 113 and the flow rate Q1 of air detected by the mass flow meter 5021.

Also, when air drawn from the atmosphere is dry, the upstream zirconia oxygen sensor 111 may be similarly dispensed with as described above.

Figure 15:
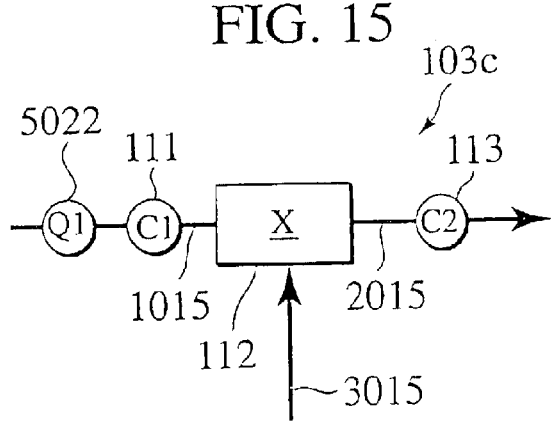
FIG. 15 is a structural view of the gas flow rate measuring device that is applied to measure the flow rate of hydrogen gas expelled from a fuel cell.

FIG. 15 is a structural view of a third concrete example 103c of the gas flow measuring device of the third embodiment.

In the present device 103c, hydrogen containing gas flowing through fuel gas supply conduits 1015, 2015 of a fuel cell electric power generation system is adopted as measuring object gas and circulated fuel gas is adopted as target gas. The present device 103c measures the flow rate q3 of hydrogen gas expelled from the fuel cell. The confluence section 112 is disposed between the fuel gas supply conduits 1015, 2015 as the gas component adjustor, and connected to the confluence section 112 is a fuel gas outlet conduit 3015 by which a fuel gas circulation path extending through the anode of the fuel cell is formed. Hydrogen containing gas is added to circulated fuel gas in the confluence 112 and supplied to the fuel cell. Disposed in the fuel gas supply conduits 1015, 2015 upstream of and downstream of the confluence section 112, respectively, are upstream and downstream zirconia oxygen sensors 111, 113. These sensors 111, 113 detect the hydrogen concentrations C1, C2 in hydrogen containing gas flowing across areas at which the sensors are installed. Also, a mass flow meter 5022 is disposed in the fuel gas supply conduit 1015 upstream of the confluence section 112 for detecting the flow rate Q1 of hydrogen containing gas.

The flow rate q3 of hydrogen gas expelled from the fuel cell can be calculated based on Eq. (1. 4). Since the flow rate Q1 of hydrogen containing gas is detected by the mass flow meter 5022 and its hydrogen concentration C1 is revealed, the flow rate q2 of hydrogen gas contained in fuel gas to be supplied to the fuel cell can be calculated in the following equation by adding flow rates of circulated component and fresh hydrogen gas with respect to one another:

$$q2 = q3 + Q1 \times C1, \tag{14}$$

Figure 16:
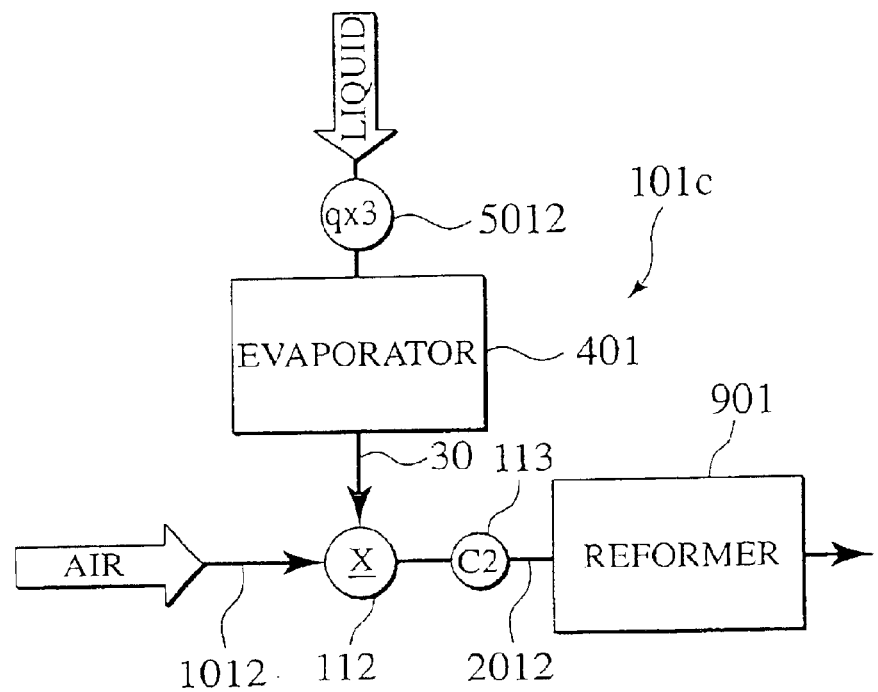
FIG. 16 is a modified form of the gas flow rate measuring device of FIG. 11 structured with no inclusion of an upstream zirconia oxygen sensor.

FIG. 16 is a structural view of a modification of the gas flow measuring device 101c of the first embodiment.

Figure 17:
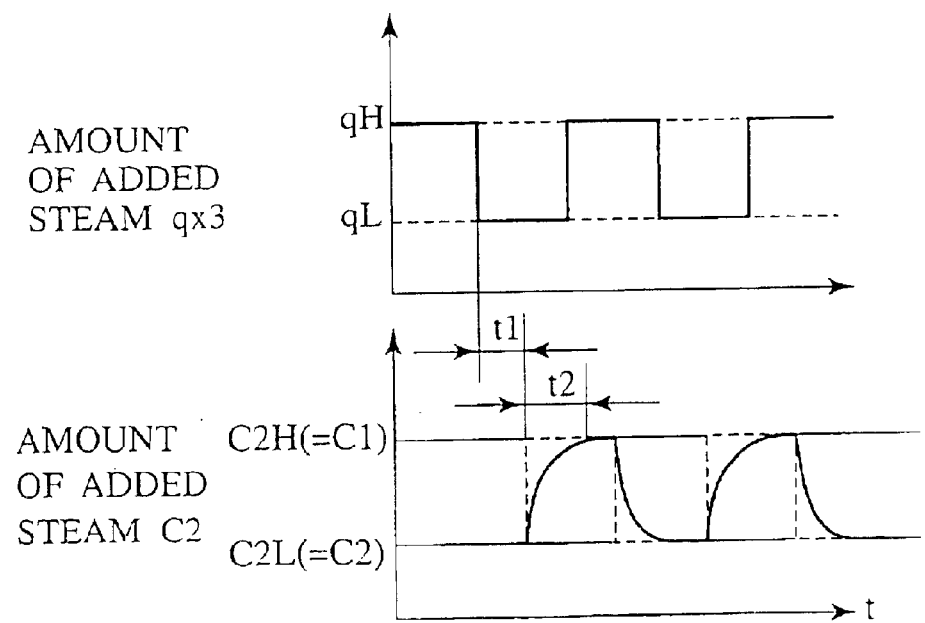
FIG. 17 is an illustrative view of a measurement principle of oxygen concentration to be performed by the gas flow rate measuring device.

The present device 101c does not include the upstream zirconia oxygen sensor 111 and is configured such that only a single zirconia oxygen sensor 113, disposed downstream of the confluence section 112, detects the oxygen concentrations C1, C2 in air before and after steam is added to air. To this end, steam is intermittently supplied to air. That is, as shown in a timing chart shown in FIG. 17, the flow rate qx3 of steam to be added is alternately switched over between zero or a small flow rate qL and a large flow rate qH. The zirconia oxygen sensor 113 detects the oxygen concentrations C2L as C2 in air with steam being added at the large flow rate qx3 and detects the oxygen concentration C2H as C1 in air under a condition where the flow rate is settled at the flow rate of zero or at the small flow rate with addition of steam being stopped. The flow rate qx3 of steam is detected by the mass flow meter 5012 that detects the flow rate qx3 of water to be supplied to the evaporator 401.

The flow rate q2 of oxygen gas to be supplied to the reformer 901 equals to the flow rate q1 of oxygen gas in air before steam is added thereto and can be calculated by Eq. (2. 3). Also, the flow rate qx1 of steam in the upstream of the confluence section 112 can be calculated as qx1=Q1−q1−3.77×q1 on supposition that the mixture ratio of 1:3.77 between oxygen gas and nitrogen gas in air. The flow rate qx2 of steam in the downstream of the confluence section 112 can be calculated by adding the flow rates qx1 and qx3 (qx2=qx1+qx3).

With the present device 101c, the single zirconia oxygen sensor 113 is used and the functions of the first and second gas concentration detection means are realized, thereby enabling detection of the oxygen concentrations C1, C2 in air before and after steam is added thereto.

The entire content of Japanese Patent Applications No. P2002-242316 with a filing date of Aug. 22, 2002 and No. P2003-37014 with a filling fate of Feb. 14, 2003 is herein incorporated by reference.

Although the present invention has been described above by reference to certain embodiments of the invention, the invention is not limited to the embodiments described above and modifications will occur to those skilled in the art, in light of the teachings. The scope of the invention is defined with reference to the following claims.

What is claimed is:

1. A gas flow measuring device comprising:
   a gas component adjustor adding target gas, composed of specific gas component contained in measuring object gas or gas differing from the specific gas component to the measuring object gas, or extracting the target gas from the measuring object gas;
   a first gas concentration detector detecting a concentration of the specific gas component of the measuring object gas prevailing upstream of the gas component adjustor or setting the concentration at a predetermined level;
   a second gas concentration detector detecting a concentration of the specific gas component of the measuring object gas prevailing downstream of the gas component adjustor; and
   a gas flow rate calculator calculating at least one of the flow rate of the measuring object gas and the flow rate of the specific gas component on the basis of the concentration of the specific gas component that is detected or set by the first gas concentration detector and the concentration of the specific gas component detected by the second gas concentration detector, and the amount of the target gas added to or extracted from the measuring object gas by the gas component adjustor.

2. The gas flow measuring device according to claim 1, wherein the gas component adjustor includes an electrochemical cell constructed of an electrolyte and a pair of electrodes between which the electrolyte is sandwiched.

3. The gas flow measuring device according to claim 2, wherein the electrochemical cell has the electrolyte formed of a hydrogen ion conductive electrolyte mold body or an oxygen ion electrolyte mold body.

4. The gas flow measuring device according to claim 2, further comprising:
   a controller controlling the amount of ion transportation between the electrodes in the electrochemical cell.

5. The gas flow measuring device according to claim 4, wherein the controller controls the amount of ion transportation in response to the concentrations detected by the first and second gas concentration detectors.

6. The gas flow measuring device according to claim 2, wherein the first and second concentration detectors include electrochemical cells, whose electrolytes are integrally formed with the electrolyte of the gas component adjustor.

7. The gas flow measuring device according to claim 1, further comprising:
   a mixer disposed between the gas component adjustor and the second gas concentration detector and mixing the measuring object gas.

8. The gas flow measuring device according to claim 1, further comprising:
   a circulator that, when gas component is extracted from the measuring object gas by the gas component adjustor, circulates extracted gas component to the measuring object gas.

9. The gas flow measuring device according to claim 1, further comprising:
   a supplier that, when gas component is added to the measuring object gas by the gas component adjustor, extracts added gas component from the measuring object gas and supplies the extracted gas component to the gas component adjustor.

10. The gas flow measuring device according to claim 2, wherein the gas component adjustor includes a fuel cell as the electrochemical cell.

11. The gas flow measuring device according to claim 2, wherein the gas component adjustor is disposed in a fuel cell system having a fuel cell, serving as an electric power supply, and includes a separate fuel cell, as the electrochemical cell, disposed upstream of the fuel cell.

12. The gas flow measuring device according to claim 1, further comprising:
a measuring object gas flow passage supplying a portion of the measuring object gas into the first gas concentration detector, the gas component adjustor and the second gas concentration detector.

13. The gas flow measuring device according to claim 12, wherein the gas flow rate calculator stores a predetermined ratio of diverged component of the measuring object gas to be directed to the measuring object gas flow passage.

14. The gas flow measuring device according to claim 12, further comprising:
a variable unit varying a ratio of diverged component of the measuring object gas to be supplied to the measuring object gas flow passage.

15. The gas flow measuring device according to claim 1, wherein the specific gas component includes at least one of oxygen and hydrogen.

16. The gas flow measuring device according to claim 1, wherein the gas component adjustor intermittently adds the target gas to the measuring object gas or intermittently extracts the target gas from the measuring object gas, and the second gas concentration detector detects the concentration of the specific gas prevailing upstream of the gas component adjustor during a phase in which the target gas is added to or extracted from the measuring object gas while the second gas concentration detector detects the concentration of the specific gas component prevailing downstream of the gas component adjustor during a phase in which the target gas is added to or extracted from the measuring object gas.

17. A gas flow measuring device comprising:
a gas component adjustor adding target gas composed of specific gas component contained in measuring object gas or gas differing from the specific gas component to the measuring object gas, or extracting the target gas from the measuring object gas;
a first gas concentration detector detecting a concentration of the specific gas component of the measuring object gas prevailing upstream of the gas component adjustor or setting the concentration at a predetermined level;
a second gas concentration detector detecting a concentration of the specific gas component of the measuring object gas prevailing downstream of the gas component adjustor;
a flow detector detecting the flow rates of the measuring object gas and the specific gas component before the target gas is added to or extracted from the measuring object gas or after the target gas is added to or extracted from the measuring object gas by the gas component adjustor; and
a gas flow rate calculator calculating the amount of the target gas, added to or extracted from the measuring object gas by the gas component adjustor, on the basis of the concentration of the specific gas component, that is detected or set by the first gas concentration detector, and the concentration of the specific gas component detected by the second gas concentration detector, and the flow rate of the measuring object gas or the flow rate of the specific gas component detected by the flow detector.

18. The gas flow measuring device according to claim 17, wherein the flow detector detects the flow rate of the measuring object gas before the target gas is added to or extracted from the measuring object gas by the gas component adjustor, and
the gas flow rate calculator adds the flow rate of the target gas, added to or extracted from the measuring object gas by the gas component adjustor, to the flow rate of the measuring object gas detected by the flow detector and calculates the flow rate of the measuring object gas after the target gas is added to or extracted from the measuring object gas by the gas component adjustor.

19. The gas flow measuring device according to claim 17, wherein the measuring object gas includes air, and the gas component adjustor adds steam as the target gas to the measuring object gas whereupon the gas flow rate calculator calculates the flow rate of added steam.

20. The gas flow measuring device according to claim 19, wherein the first and second gas concentration detectors detect the concentration of oxygen gas as the specific gas.

21. The gas flow measuring device according to claim 19, wherein the air containing steam added by the gas component adjustor is supplied to a fuel reformer of a fuel cell electric power generation system.

22. The gas flow measuring device according to claim 19, wherein the air containing steam added by the gas component adjustor is supplied to a cathode of a fuel cell.

23. The gas flow measuring device according to claim 17, wherein the measuring object gas includes hydrogen gas as the specific gas, and the first and second gas concentration detectors detect the concentration of the hydrogen gas.

24. The gas flow measuring device according to claim 23, wherein the measuring object gas includes fuel gas supplied to an anode of a fuel cell.

25. The gas flow measuring device according to claim 23, wherein the gas component adjustor adds steam as the target gas to the measuring object gas, and the gas flow rate calculator calculates the flow rate of added steam.

26. The gas flow measuring device according to claim 19, wherein the gas component adjustor evaporates water into steam and adds the steam to the measuring object gas.

27. The gas flow measuring device according to claim 19, wherein each of the first and gas concentration detectors comprises a zirconia oxygen sensor.

28. The gas flow measuring device according to claim 17, wherein the gas component adjustor intermittently adds the target gas to the measuring object gas or intermittently extracts the target gas from the measuring object gas, and the second gas concentration detector detects the concentration of the specific gas prevailing upstream of the gas component adjustor during a phase in which the target gas is added to or extracted from the measuring object gas while the second gas concentration detector detects the concentration of the specific gas prevailing downstream of the gas component adjustor during a phase in which the target gas is added to or extracted from the measuring object gas.

29. A method of measuring object gas flow, the method comprising: adding target gas composed of specific gas component contained in measuring object gas or gas differing from the specific gas component to the measuring object gas, or extracting the target gas from the measuring object gas;

detecting a concentration of the specific gas component before the target gas is added to or extracted from the measuring object gas and detecting the concentration of the specific gas component of the measuring object gas prevailing downstream thereof after the target gas has been added to or extracted from the measuring object gas; and calculating at least one of the flow rate of the measuring object gas and the flow rate of the specific gas component on the basis of the detected concentrations of the specific gas component and the amount of the target gas added to or extracted from the measuring object gas.

30. A method of measuring object gas flow, the method comprising:

adding specific gas contained in measuring object gas or target gas composed of gas differing from the specific gas to the measuring object gas, or extracting the target gas from the measuring object gas;

detecting a concentration of the specific gas component before the target gas is added to or extracted from the measuring object gas and detecting the concentration of the specific gas component of the measuring object gas prevailing downstream thereof after the target gas has been added to or extracted from the measuring object gas;

detecting the flow rates of the measuring object gas or the specific gas component before the target gas is added to or extracted from the measuring object gas or after the target gas has been added to or extracted from the measuring object gas; and calculating the amount of the target gas, added to or extracted from the measuring object gas, on the basis of the detected concentrations of the specific gas component and the flow rate of the measuring object gas or the flow rate of the specific gas component.

31. A gas flow measuring device comprising:

gas component adjusting means for adding target gas composed of specific gas component contained in measuring object gas or gas differing from the specific gas component to the measuring object gas, or extracting the target gas from the measuring object gas;

first gas concentration detecting means for detecting a concentration of the specific gas component of the measuring object gas prevailing upstream of the gas component adjustor or setting the concentration at a predetermined level;

second gas concentration detecting means for detecting a concentration of the specific gas component of the measuring object gas prevailing downstream of the gas component adjustor; and gas flow rate calculating means for calculating at least one of the flow rate of the measuring object gas and the flow rate of the specific gas component on the basis of the concentration of the specific gas component that is detected or set by the first gas concentration detecting means and the concentration of the specific gas component detected by the second gas concentration detecting means, and the amount of the target gas added to or extracted from the measuring object gas by the gas component adjusting means.

32. A gas flow measuring device comprising:

gas component adjusting means for adding target gas composed of specific gas component contained in measuring object gas or gas differing from the specific gas component to the measuring object gas, or extracting the target gas from the measuring object gas;

first gas concentration detecting means for detecting a concentration of the specific gas component of the measuring object gas prevailing upstream of the gas component adjustor or setting the concentration at a predetermined level;

second gas concentration detecting means for detecting a concentration of the specific gas component of the measuring object gas prevailing downstream of the gas component adjustor;

flow detecting means for detecting the flow rates of the measuring object gas and the specific gas component before the target gas is added to or extracted from the measuring object gas or after the target gas is added to or extracted from the measuring object gas by the gas component adjustor; and gas flow rate calculating means for calculating the amount of the target gas, added to or extracted from the measuring object gas by the gas component adjusting means, on the basis of the concentration of the specific gas component, that is detected or set by the first gas concentration detecting means, and the concentration of the specific gas component detected by the second gas concentration detecting means, and the flow rate of the measuring object gas or the flow rate of the specific gas component detected by the flow detecting means.

* * * * *